US008257949B2

(12) United States Patent
Wakarchuk et al.

(10) Patent No.: US 8,257,949 B2
(45) Date of Patent: Sep. 4, 2012

(54) SELF-PRIMING POLYSIALYLTRANSFERASE

(75) Inventors: Warren Wakarchuk, Ottawa (CA); Michel Gilbert, Gatineau (CA)

(73) Assignee: National Research Council of Canada, Ottawa, Ontario (CA)

( * ) Notice: Subject to any disclaimer, the term of this patent is extended or adjusted under 35 U.S.C. 154(b) by 608 days.

(21) Appl. No.: 12/162,721

(22) PCT Filed: Jan. 30, 2007

(86) PCT No.: PCT/CA2007/000131
§ 371 (c)(1),
(2), (4) Date: Oct. 30, 2008

(87) PCT Pub. No.: WO2007/087711
PCT Pub. Date: Aug. 9, 2007

(65) Prior Publication Data

US 2009/0246832 A1 Oct. 1, 2009

Related U.S. Application Data

(60) Provisional application No. 60/764,171, filed on Jan. 31, 2006.

(51) Int. Cl.
*C12P 19/26* (2006.01)

(52) U.S. Cl. ........... 435/84; 435/193; 435/320.1; 435/2; 435/252.33

(58) Field of Classification Search ........................ None
See application file for complete search history.

(56) References Cited

U.S. PATENT DOCUMENTS

| | | | |
|---|---|---|---|
| 6,503,744 | B1 | 1/2003 | Gilbert et al. |
| 6,699,705 | B2 | 3/2004 | Gilbert et al. |

FOREIGN PATENT DOCUMENTS

| | | | |
|---|---|---|---|
| WO | WO 99/31224 A2 | 6/1999 | |
| WO | WO 00/46379 A1 | 8/2000 | |

OTHER PUBLICATIONS

Gilbert, M et al, "The synthesis of sialylated oligosaccharides using a CMP-Neu5Ac synthetase/sialyltransferase fusion," Nature Biotechnology, Aug. 1, 1998, pp. 769-772, vol. 16, No. 8.

Steenbergen, S et al, "Functional relationships of the sialyltransferases involved in expression of the polysialic acid capsules of *Escherichia coli* K1 and K92 and Neisseria meningitidis groups B or C." J. of Biological Chem., Apr. 25, 2003, pp. 15349-15359, vol. 278, No. 17.

Willis, L et al, "Characterization of the alpha-2,8-polysialyltransferase from Neisseria menigitidis with synthetic acceptors, and the development of a self-priming polysialyltransferase fusion enzyme." Glycobiology, Nov. 13, 2007, pp. 177-186, vol. 18, No. 2.

Angata et al., "ST8Sia II and ST8Sia IV polysialyltransferases exhibit marked differences in utilizing various acceptors containing oligosialic acid and short polsialic acid. The basis for cooperative polysialylation by two enzymes," *J. Biol. Chem.* 277:36808-36817 (2002).

Angata et al., "Molecular dissection of the ST8Sin IV polysialyltransferase. Distinct domains are required for neural cell adhesion molecule recognition and polysialylation," *J. Biol. Chem.* 279:25883-25890 (2004).

Cho and Troy, "Polysialic acid engineering: synthesis of polysialylated neoglycosphingolipids by using the polysialyltransferase from neuroinvasive *Escherichia coli* K1," *Proc. Natl. Acad. Sci. USA* 91:11427-11431 (1994).

Close et al., "Polysialyltransferase-1 autopolysialylation is not requisite for polysialylation of neural cell adhesion molecule," *J. Biol. chem.* 275:4484-4491 (2000).

Close et al., "The polysialyltransferase ST8Sia ILSTX: post-translational processing and role of autoploysialylation in the polysialylation of neural cell adhesion molecule," *Glycobiology* 11:997-1008 (2001).

Muhlenhoff et al., "The impact of *N*-glycosylation on the functions of polysialyltransferases," *J. Biol. Chem.* 276:34066-34073 (2001).

Shen et al., "Expression of α2,8/2,9-polysialyltransferase from *Escherichia coli* K92. Characterization of the enzyme and its reaction products," *J. Biol. Chem.* 274:35139-35146 (1999).

*Primary Examiner* — Hope Robinson
(74) *Attorney, Agent, or Firm* — Nada Jain, P.C.

(57) ABSTRACT

The invention relates to a fusion protein comprising a bifunctional sialytransferase and a poly-sialytransferase and methods to use the fusion proteins for production of poly-sialylated end products, e.g. oligosaccharides and glycoproteins.

15 Claims, 13 Drawing Sheets

Self-priming poly-sialyltransferase DNA sequence
Cst-II OH4384 is 5' italicized sequence
glycine linker is underlined and bold
Pst ttom N meningitidis 992B is sequence 3' of the linker

FIG. 3A

*5'ATGAAAAAAGTTATTATTGCTGGAAATGGACCAAGTTTAAAAGAAATTGATTATTCAAGACTACCAAATGA*
*TTTTGATGTATTTAGATGTAATCAATTTTATTTTGAAGATAAATACTATCTTGGTAAAAAATGCAAGGCAGTA*
*TTTTACAATCCTAGTCTTTTTTTTGAACAATACTACACTTTAAAACATTTAATCCAAAATCAAGAATATGAGAC*
*CGAACTAATTATGTGTTCTAATTACAACCAAGCTCATCTAGAAAATGAAAATTTTGTAAAAACTTTTTACGAT*
*TATTTTCCTGATGCTCATTTGGGATATGATTTTTTCAAACAACTTAAAGATTTTAATGCTTATTTTAAATTTCA*
*CGAAATTTATTTCAATCAAAGAATTACCTCAGGGGTCTATATGTGTGCAGTAGCCATAGCCCTAGGATACA*
*AAGAAATTTATCTTTCGGGAATTGATTTTTATCAAAATGGGTCATCTTATGCTTTTGATACTAAACAAAAAAA*
*TCTTTTAAAATTGGCTCCTAATTTTAAAAATGATAATTCACACTATATTGGACATAGTAAAAATACAGATATAA*
*AAGCTTTAGAATTTCTAGAAAAAACTTACAAAATAAAACTATATTGCTTATGTCCTAACAGTCTTTTAGCAAA*
*TTTTATAGAACTAGCGCCAAATTTAAATTCAAATTTTATCATACAAGAAAAAAATAACTACACTAAAGATATA*
*CTCATACCTTCTAGTGAGGCTTATGGAAAATTTTCAAAAAATATTAATTTT*<u>GGAGGCGGACAT</u>ATGCTAA
AGAAAATAAAAAAAGCTCTTTTTCAGCCTAAAAAGTTTTTTCAAGATTCAATGTGGTTGACAACAT
CTCCATTTTATCTTACCCCCCCACGTAACAATTTATTTGTCATATCTAATTTAGGTCAGCTTAACCA
AGTCCAAAGCCTAATTAAAATACAAAAATTAACCAATAATTTACTAGTAATTTTATATACTTCTAA
AAACTTAAAAATGCCTAAGTTAGTTCATCAATCAGCTAACAAGAATCTATTTGAATCTATTTATCT
ATTTGAGCTTCCTAGAAGCCCTAATAATATAACTCCTAAAAAATTACTTTATATTTATAGAAGTTAC
AAAAAAATCCTTAATATTATACAGCCTGCTCATCTCTATATGCTGTCTTTTACAGGCCACTACTCCT
ATCTGATTAGTATTGCAAAGAAGAAGAATATTACGACTCATTTAATTGATGAAGGGACTGGAACA
TACGCTCCTTTATTAGAATCATTTTCATATCATCCAACAAAATTAGAACGTAATTTGATTGGAAATA
ATCTTAATATTAAAGGATATATAGATCATTTTGACATATTGCATGTCCCCTTTCCTGAATATGCTAA
AAAAATATTTAATGCAAAAAAATATAACGGGTTTTTTGCGCATGCTGGAGGAATAAGCATTAATA
ATAACATTGCAAACTTACAGAAAAAATATCAAATATCTAAAAATGACTATATTTTTGTTAGTCAAC
GCTACCCCATTTCAGATGATTTGTATTATAAGAGTATAGTAGAAATCTTAAACAGCATAAGTTTAC
AAATTAAAGGAAAGATATTTATTAAACTACACCCAAAAGAGATGGGCAACAACTATGTAATGTCT
TTATTTCTAAATATGGTAGAAATAAACCCTCGGCTGGTAGTTATTAATGAACCTCCTTTTCTAATTG
AGCCCCTAATATACTTAACAAATCCTAAAGGAATTATAGGCCTGGCCTCTAGTTCTTTAATTTATAC
ACCATTACTCTCACCCTCAACCCAATGTCTTTCTATTGGAGAGTTAATTATTAACTTAATTCAAAAA
TATTCAATGGTGGAAAACACTGAAATGATCCAAGAACACTTAGAGATTATTAAGAAATTTAATTTT
ATTAATATACTAAATGATTTAAATGGGGTAATAAGTAACCCCCTCTTTAAAACAGAAGAAACATTT
GAAACACTTCTTAAATCTGCAGAATTCGCATATAAATCTAAAAACTACTTTCAGGCTATTTTTTACT
GGCAACTTGCCAGCAAAAACAATATTACCTTATTAGGGCACAAAGCATTATGGTACTACAATGCA
CTTTATAATGTAAAACAAATTTATAAGATGGAATATTCAGATATTTTTTATATCGATAATATCTCCG
TAGACTTTCATAGTAAAGATAAATTGACATGGGAAAAAATTAAACATTATTACTATTTCGCCGACA
ATAGAATTGGTAGAGATAGATAATAG 3'

FIG. 3B

Self-priming poly-sialyltransferase amino acid sequence
Cst-II OH4384 is amino-terminal italicized sequence
glycine linker is underlined and bold
Pst from *N. meningitidis* 992B follows the linker

*MKKVIIAGNGPSLKEIDYSRLPNDFDVFRCNQFYFEDKYYLGKKCKAVFYNP*
*SLFFEQYYTLKHLIQNQEYETELIMCSNYNQAHLENENFVKTFYDYFPDAHL*
*GYDFFKQLKDFNAYFKFHEIYFNQRITSGVYMCAVAIALGYKEIYLSGIDFYQ*
*NGSSYAFDTKQKNLLKLAPNFKNDNSHYIGHSKNTDIKALEFLEKTYKIKLY*
*CLCPNSLLANFIELAPNLNSNFIIQEKNNYTKDILIPSSEAYGKFSKNINF*<u>GG</u>
<u>GH</u>MLKKIKKALFQPKKFFQDSMWLTTSPFYLTPPRNNLFVISNLGQLNQV
QSLIKIQKLTNNLLVILYTSKNLKMPKLVHQSANKNLFESIYLFELPRSPN
NITPKKLLYIYRSYKKILNIIQPAHLYMLSFTGHYSYLISIAKKKNITTHLI
DEGTGTYAPLLESFSYHPTKLERNLIGNNLNIKGYIDHFDILHVPFPEYAK
KIFNAKKYNRFFAHAGGISINNNIANLQKKYQISKNDYIFVSQRYPISDDL
YYKSIVEILNSISLQIKGKIFIKLHPKEMGNNYVMSLFLNMVEINPRLVVI
NEPPFLIEPLIYLTNPKGIIGLASSSLIYTPLLSPSTQCLSIGELIINLIQKYS
MVENTEMIQEHLEIIKKFNFINILNDLNGVISNPLFKTEETFETLLKSAEFA
YKSKNYFQAIFYWQLASKNNITLLGHKALWYYNALYNVKQIYKMEYSDI
FYIDNISVDFHSKDKLTWEKIKHYYYFADNRIGRDR

Starting material (▨), +1 NeuAc (▧), +2 NeuAc (□), +3 NeuAc (▥), +4 NeuAc (☒), >4 NeuAc (▩).

Figure 11:
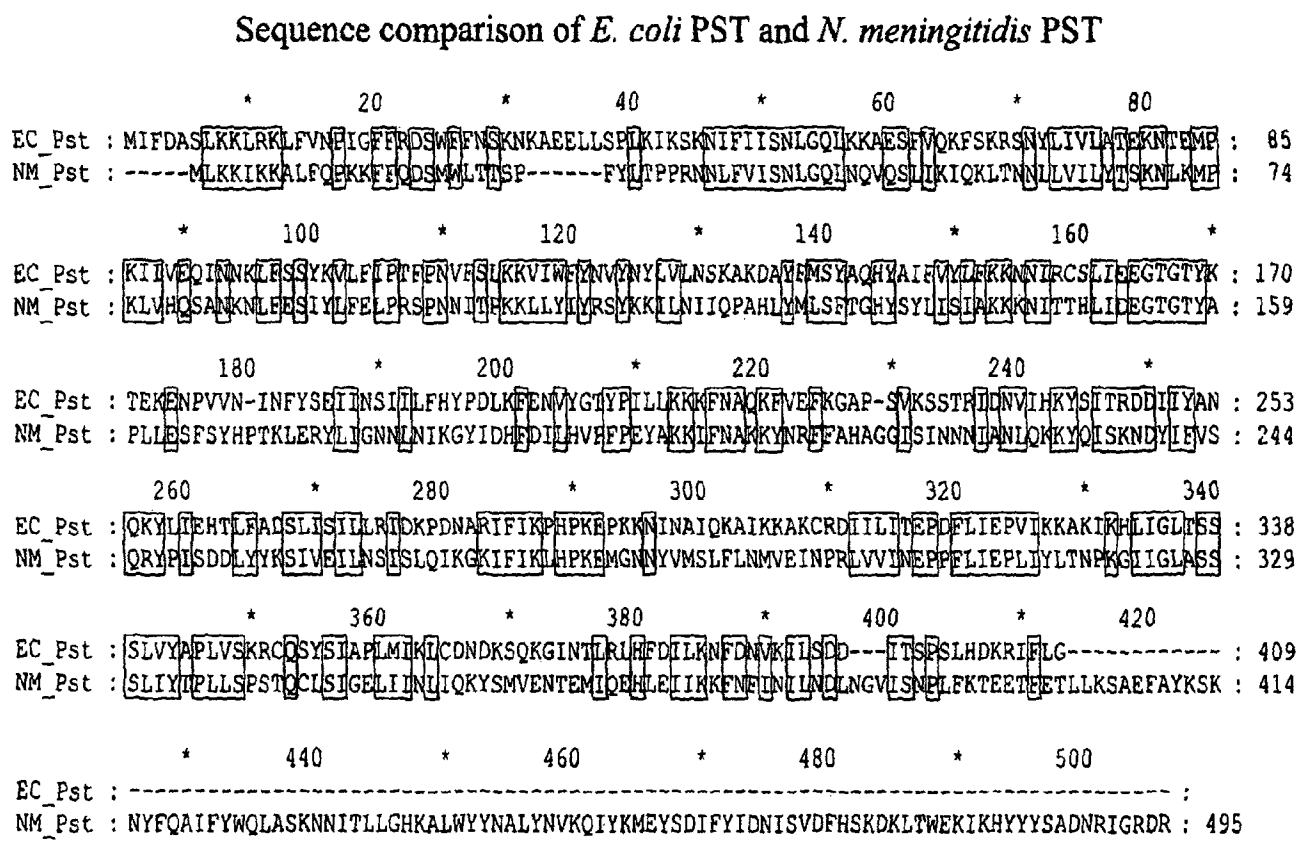

Sequence comparison of *E. coli* PST and *N. meningitidis* PST

```
                     *        20         *        40         *        60         *        80
EC_Pst : MIFDASLKKLRKLFVNPIGFFRDSWFFNSKNKAEELLSPLKIKSKNIFIISNLGQLKKAESFVQKFSKRSNYLIVLATEKNTEMP :  85
NM_Pst : -----MLKKIKKALFQPKKFFQDSMWLTTSP------FYLTPPRNNLFVISNLGQLNQVQSLIKIQKLTNNLLVILYTSKNLKMP :  74

                  *       100         *       120         *       140         *       160         *
EC_Pst : KIIVEQINNKLFSSYKVLFIPTFPNVFSLKKVIWFYNVYNYLVLNSKAKDAYFMSYAQHYAIFVYLFKKNNIRCSLIEEGTGTYK : 170
NM_Pst : KLVHQSANKNLFESIYLFELPRSPNNITPKKLLYIYRSYKKILNIIQPAHLYMLSFTGHYSYLISIAKKKNITTHLIDEGTGTYA : 159

              180         *       200         *       220         *       240         *
EC_Pst : TEKENPVVN-INFYSEIINSIILFHYPDLKFENVYGIYPILLKKKFNAQKFVEFKGAP-SVKSSTRIDNVIHKYSITRDDIIYAN : 253
NM_Pst : PLLESFSYHPTKLERYLIGNNLNIKGYIDHFDILHVPFPEYAKKIFNAKKYNRFFAHAGGISINNNIANLQKKYQISKNDYIEVS : 244

          260         *       280         *       300         *       320         *       340
EC_Pst : QKYLIEHTLFADSLISILLRIDKPDNARIFIKPHPKEPKKNINAIQKAIKKAKCRDIILITEPDFLIEPVIKKAKIKHLIGLTSS : 338
NM_Pst : QRYPISDDLYYKSIVEILNSISLQIKGKIFIKLHPKEMGNNYVMSLFLNMVEINPRLVVINEPPFLIEPLIYLTNPKGIIGLASS : 329

                   *       360         *       380         *       400         *       420
EC_Pst : SLVYAPLVSKRCQSYSIAPLMIKICDNDKSQKGINTLRLHFDILKNFDNVKIILSDD---ITSPSLHDKRIFLG------------ : 409
NM_Pst : SLIYTPLLSPSTQCLSIGELIINLIQKYSMVENTEMIQEHLEIIKKFNFINIINDLNGVISNPLFKTEETFETLLKSAEFAYKSK : 414

                  *       440         *       460         *       480         *       500
EC_Pst : ---------------------------------------------------------------------------------- :
NM_Pst : NYFQAIFYWQLASKNNITLLGHKALWYYNALYNVKQIYKMEYSDIFYIDNISVDFHSKDKLTWEKIKHYYYSADNRIGRDR : 495
```

Nucleic acid encoding PST-16 fusion protein: sequence of *E. coli* PST is in normal text; sequence of Cst-II from OH4384 is italicized; linker sequence is underlined and in bold.

5'
*ATGAAAAAAGTTATTATTGCTGGAAATGGACCAAGTTTAAAAGAAATTGATTATTCAAGACTACCAAATGATT*
*TTGATGTATTTAGATGTAATCAATTTTATTTTGAAGATAAATACTATCTTGGTAAAAAATGCAAGGCAGTATT*
*TTACAATCCTAGTCTTTTTTTTGAACAATACTACACTTTAAAACATTTAATCCAAAATCAAGAATATGAGACC*
*GAACTAATTATGTGTTCTAATTACAACCAAGCTCATCTAGAAAATGAAAATTTTGTAAAAACTTTTTACGATT*
*ATTTTCCTGATGCTCATTTGGGATATGATTTTTTCAAACAACTTAAAGATTTTAATGCTTATTTTAAATTTCAC*
*GAAATTTATTTCAATCAAAGAATTACCTCAGGGGTCTATATGTGTGCAGTAGCCATAGCCCTAGGATACAA*
*AGAAATTTATCTTTCGGGAATTGATTTTTATCAAAATGGGTCATCTTATGCTTTTGATACTAAACAAAAAAAT*
*CTTTTAAAATTGGCTCCTAATTTTAAAAATGATAATTCACACTATATTGGACATAGTAAAAATACAGATATAAA*
*AGCTTTAGAATTTCTAGAAAAAACTTACAAAATAAAACTATATTGCTTATGTCCTAACAGTCTTTTAGCAAAT*
*TTTATAGAACTAGCGCCAAATTTAAATTCAAATTTTATCATACAAGAAAAAAATAACTACACTAAAGATATAC*
*TCATACCTTCTAGTGAGGCTTATGGAAAATTTTCAAAAAATATTAATTTT*GGAGGCGGACATATGATATT
TGATGCTAGTTTAAAGAAGTTGAGGAAATTATTTGTAAATCCAATTGGGTTTTTCCGTGACTCATG
GTTTTTTAATTCTAAAAACAAGGCTGAAGAGCTACTATCACCGTTAAAAATAAAAAGTAAAAATAT
TTTTATAATTAGTAACCTGGGGCAATTAAAAAAAGCTGAGTCATTTGTACAAAAATTTAGCAAGAG
AAGTAACTATCTTATTGTTTTGGCAACTGAAAAAAATACTGAGATGCCAAAAATTATTGTTGAACA
AATAAATAATAAATTATTTTCTTCATACAAGGTACTATTCATTCCAACTTTCCCAAATGTTTTTTCA
CTTAAAAAGGTTATATGGTTTTATAACGTATATAATTATTTAGTTTTAAATTCAAAAGCTAAAGAT
GCTTATTTTATGAGCTATGCGCAACATTATGCAATCTTCGTATATTTGTTCAAAAAAAATAATATAA
GATGTTCATTAATTGAAGAGGGGACAGGGACTTATAAAACCGAAAAAGAAAACCCAGTAGTAAAT
ATTAATTTTTATTCAGAGATTATTAATTCAATTATCTTGTTCCATTATCCAGATTTGAAATTTGAAA
ATGTATACGGTACATATCCAATTTTGCTTAAGAAAAAATTTAATGCGCAAAAATTTGTTGAGTTTA
AAGGTGCTCCATCAGTTAAATCATCAACCAGAATAGATAATGTTATCCATAAATATTCTATAACTA
GAGATGATATAATATATGCAAATCAAAAGTATTTGATTGAACATACATTATTTGCGGATTCGTTAA
TTTCTATCTTACTTAGAATAGATAAGCCTGATAATGCAAGAATATTTATAAAACCTCACCCTAAAG
AGCCTAAAAAAAATATTAATGCAATTCAAAAGGCAATAAAAAAGGCAAAAATGTCGTGACATAATT
CTTATAACAGAGCCAGACTTTTTAATAGAGCCGGTAATAAAAAAAGCAAAAATAAAACACTTAAT
TGGATTAACATCATCTTCTTTGGTATATGCACCTTTAGTTTCTAAAAGATGTCAGTCTTATTCAATA
GCGCCTCTTATGATAAAGTTGTGTGATAATGATAAATCCCAAAAAGGGATTAATACGCTGCGTCTC
CATTTCGATATTTTAAAGAATTTTGATAATGTTAAAATATTATCGGATGATATAACATCTCCCTCTT
TGCACGATAAAAGGATTTTCTTGGGGGAGTAA

FIG. 12B

PST-16 fusion protein: sequence of *E coli* PST is in normal text; sequence of Cst-II from OH4384 is italicized; linker sequence is underlined and in bold. PST methionines are in bold text.

PST-16 proteins sequence CST-II in blue, PST in black
*MKKVIIAGNGPSLKEIDYSRLPNDFDVFRCNQFYFEDKYYLGKKCKAVFYNP*
*SLFFEQYYTLKHLIQNQEYETELIMCSNYNQAHLENENFVKTFYDYFPDAHL*
*GYDFFKQLKDFNAYFKFHEIYFNQRITSGVYMCAVAIALGYKEIYLSGIDFYQ*
*NGSSYAFDTKQKNLLKLAPNFKNDNSHYIGHSKNTDIKALEFLEKTYKIKLY*
*CLCPNSLLANFIELAPNLNSNFIIQEKNNYTKDILIPSSEAYGKFSKNINF*GG
GHMIFDASLKKLRKLFVNPIGFFRDSWFFNSKNKAEELLSPLKIKSKNIFI
ISNLGQLKKAESFVQKFSKRSNYLIVLATEKNTEMPKIIVEQINNKLFSSY
KVLFIPTFPNVFSLKKVIWFYNVYNYLVLNSKAKDAYFMSYAQHYAIFV
YLFKKNNIRCSLIEEGTGTYKTEKENPVVNINFYSEIINSIILFHYPDLKFE
NVYGTYPILLKKKFNAQKFVEFKGAPSVKSSTRIDNVIHKYSITRDDIIYA
NQKYLIEHTLFADSLISILLRIDKPDNARIFIKPHPKEPKKNINAIQKAIKK
AKCRDIILITEPDFLIEPVIKKAKIKHLIGLTSSSLVYAPLVSKRCQSYSIAP
LMIKLCDNDKSQKGINTLRLHFDILKNFDNVKILSDDITSPSLHDKRIFLG
E

SELF-PRIMING POLYSIALYLTRANSFERASE

CROSS-REFERENCES TO RELATED APPLICATIONS

This application is a U.S. National Phase Application under 35 U.S.C. §371 of International Application No. PCT/CA2007/000131, filed on Jan. 30, 2007, which claims the benefit of U.S. Provisional Application No. 60/764,171, filed Jan. 31, 2006, which is herein incorporated by reference for all purposes.

FIELD OF THE INVENTION

The invention relates to a fusion protein comprising a bifunctional sialyltransferase and a poly-sialyltransferase and methods to use the fusion proteins for production of poly-sialylated end products, e.g., oligosaccharides and glycoproteins.

BACKGROUND OF THE INVENTION

Glycoproteins, glycolipids and polysaccharides are present on the cell surface of mammalian cells and are central molecules in many biological processes. They participate in cell-cell recognition, cell differentiation and various receptor-ligand interactions throughout biology. Many of these biologically active glycans contain an essential 9-carbon sugar that is known as sialic acid, or N-acetyl-neuraminic acid (NeuAc).

Some bacterial pathogens that invade the mammalian host have taken advantage of the presence of sialic acid containing glycoconjugates on the host. These bacteria display some of these same carbohydrate chains on bacterial cell surfaces, and indeed a role for these carbohydrates in pathogenesis has been demonstrated. See, e.g., Kahler, C. M. and Stephens, D. S., *Crit Rev Microbiol,* 24:281-334 (1998), and Moran, A. P. et al., *FEMS Immunol Med Microbiol,* 16:105-115 (1996). It is thought that the presence of the carbohydrate mimics allows the pathogens to escape detection by the immune system since these molecules are not considered foreign. Further, the presence of these carbohydrates presents a physical barrier for the killing action of serum complement See, e.g., Vogel, U. et al., *Med Microbiol Immunol* (*Berl*), 185:81-87 (1996). Finally it may be mat certain pathogens use normal human receptors that recognise their surface carbohydrate structures as a means of aiding transmission (or colonization of the host, although this mechanism remains unproven for many of these pathogens). See, e.g., Preston, A. et al., *Crit Rev Microbiol,* 22:139-180 (1996) and Harvey, H. A. et al., *Mol Microbiol,* 36:1059-1070 (2000).

Capsular polysaccharides from group B *Neisseria meningitidis* and *Escherichia coli* K1 have sialic acid in linkages that are molecular mimics of the polysialic acid (PSA) structure seen mainly in the mammalian neural cell adhesion molecule, a brain specific protein integral to neuronal function. Thus they are found as a homo-polymer of α-2,8-linked Neu5Ac, and also as homo-polymers of α-2,9-linked residues, as a co-polymer in which the linkage is mixed α-2,8/α-2,9, and finally as polymers in which other sugars are included, as in the group B *Streptococcus agalactiae*. These polysialic acid capsules are required for neuro-invasive disease in the case of *E. coli, N. meningitidis* and *P. haemolytica*. See, e.g., Silver, R. P. a. V. E. R. (1990) in Vol. XI (Iglewski, B. H. a. C. V. L., Ed.) pp 39-60, Academic Press, San Diego. It is important to note that because many of these pathogens are specific for a human host, data from animal model infections may not have shown all of the true functions of these glycoconjugates.

To date there has been little detailed work on the fundamental aspects of the sialyltransferase enzymology from bacterial pathogens. We and others (Gilbert, M. et al., *J Biol Chem,* 271:28271-28276 (1996)) (Gilbert, M. et al., *J Biol Chem,* 275:3896-3906 (2000)) (Chiu, C. P. et al., *Nat. Struct. Mol. Biol.,* 11:163-170 (2004)) (Yu, H. et al., *J. Am. Chem. Soc.,* 127:17618-17619 (2005)) have shown that It is possible to express, purify and crystallize some of those enzymes responsible for LOS sialylation. See, e.g., Gilbert, M. et al., *J Biol Chem,* 271:28271-28276 (1996); Gilbert, M. et al., *J Biol Chem,* 275:3896-3906 (2000); Chiu, C. P. et al., *Nat. Struct. Mol. Biol.,* 11:163-170 (2004); and Yu, H. et al., *J. Am. Chem. Soc.,* 127:17618-17619 (2005). However no such work has been done with those enzymes involved in the generation of the sialic acid homopolymeric capsules.

The genetic loci for the PSA capsule production have been identified in both *E. coli* and *N. meningitidis*, and some work has been done on the recombinant enzymes (NeuS) from *E. coli* K1, and K92. See, e.g., Cho, J. and Troy F A, I. I., *PNAS,* 91:11427-11431 (1994) and Shen, G. J. et al., *J. Biol. Chem.,* 274:35139-35146 (1999). But again no detailed enzymology on the isolated sialyltransferase has been reported. The study of the enzymology has been hampered by the inability to isolate soluble enzyme, and the lack of a simple synthetic acceptor from which enzymology data could be obtained. Thus, production of polysialic acid conjugates in vitro has been hampered. The present invention solves this and other needs.

BRIEF SUMMARY OF THE INVENTION

In one aspect, the invention provides a self-pruning polysialyltransferase protein that is a fusion of a bi-functional sialyltransferase and a poly-sialyltransferase. The self-priming poly-sialyltransferase protein transfers a multitude of sialic acid moieties from a donor substrate to an acceptor substrate to produce a poly-sialylated product that has at least three sialic acid moieties.

In one embodiment, the self-priming poly-sialyltransferase produces an oligosaccharide that has at least five, nine, or twelve sialic acid moieties. In another embodiment, the self-priming poly-sialyltransferase protein transfers a first sialic acid moiety to a terminal galactose on the acceptor substrate. In a further embodiment, the self-priming polysialyltransferase protein produces a homo-polymer of α-2,8-linked sialic acid moieties, a homo-polymer of α-2,9-linked sialic acid moieties or a co-polymer of α-2,8/α-2,9-linked sialic acid moieties.

In one embodiment, the invention provides a self-priming poly-sialyltransferase protein is a fusion of a bacterial bi-functional sialyltransferase protein and a bacterial poly-sialyltransferase protein. In another embodiment, the self-priming poly-sialyltransferase protein includes a polysialyltransferase protein from *E. coli* or *Neisseria*. In a further embodiment, the self-priming poly-sialyltransferase protein includes any one of the following poly-sialyltransferase proteins: SEQ ID NO:3, 4, 5, 6, and 7; which is fused to any one of the following bi-functional sialyltransferase proteins: SEQ ID NO:8, 9, 10, 11, 12, and 13. In another embodiment, the self-priming poly-sialyltransferase protein includes a bi-functional sialyltransferase protein from *Campylobacter.*

In one embodiment, the invention provides a self-priming poly-sialyltransferase protein includes an amino acid sequence with at least 80%, 90%, or 95% identity to SEQ ID NO:3.

In one embodiment, the invention provides a self-priming poly-sialyltransferase protein that is part of a reaction mixture, that e.g., also includes appropriate substrates.

In one embodiment, the invention provides a nucleic acid that encodes the self-priming poly-sialyltransferase protein. In another embodiment, the nucleic acid is part of an expression vector. In a further embodiment, the expression vector is found in a host cell.

In another aspect the invention provides a method of producing a poly-sialylated oligosaccharide product, by contacting an acceptor substrate comprising an oligosaccharide with the self-priming poly-sialyltransferase protein and with a donor substrate comprising a sialic acid moiety; and then allowing transfer of at least three sialic acid moieties from the donor substrate to the acceptor substrate, thereby producing the poly-sialylated oligosaccharide product. If the acceptor substrate has a single terminal sialic acid moiety, at least two sialic acid moieties are transferred. If the acceptor substrate has two terminal sialic acid moieties, at least one sialic acid moiety is transferred.

In one embodiment, the invention provides a method that produces a poly-sialylated oligosaccharide product that has at least five, nine, or twelve sialic acid moieties. In another embodiment, the acceptor substrate is a glycoprotein. In a further embodiment, the acceptor substrate comprises a terminal galactose. The poly-sialylated product can include e.g., a homo-polymer of α-2,8-linked sialic acid moieties, a homo-polymer of α-2,9-linked sialic acid moieties, or a co-polymer of α-2,8/α-2,9-linked sialic acid moieties. The method can also include an additional step of isolating the poly-sialylated product. In another embodiment, the method is performed at a commercial scale of production of the poly-sialylated product.

BRIEF DESCRIPTION OF THE DRAWINGS

FIG. 3A shows the nucleic acid sequence of PST-17 (SEQ ID NO:1), which encodes a self-priming poly-sialyltransferase protein. The protein is a fusion of a truncated bi-functional α-2,3/α-2,8-sialyltransferase (Cst-II protein from *C. jejuni*) and a poly-sialyltransferase (Pst from *N. meningitidis* strain 992B). The Cst-II sequence begins at the 5' end and is italicized. An amino acid linker between the two enzymes is underlined and in bold. The remaining sequence through the 3' end is the *Neisseria* Pst.

FIG. 3B shows the amino acid sequence of the PST-17 self-priming polysialyltransferase protein (SEQ ID NO:2). The Cst-II sequence begins at the amino terminus and is italicized. An amino acid linker between the two enzymes is underlined and in bold. The remaining sequence through the carboxy terminus is the *Neisseria* Pst.

FIG. 9 provides a comparison of polysialic acid synthesis activity using a mixture of unfused Cst-II and PST-13 enzymes or the PST-17 fusion enzyme. The sialic acid acceptor was the glycopeptide interferon α2b-[TAg]-FCHASE.

FIG. 10 provides provides a comparison of polysialic acid synthesis activity using a mixture of unfused Cst-II and PST-13 enzymes or the PST-17 fusion enzyme. The sialic acid acceptor was the mono-sialylated glycopeptide interferon α2b-[S-TAg]-FCHASE.

FIG. 11 provides an alignment of polysialyltransferase proteins from *E. coli* (top; SEQ ID NO:7) and *N. meningitides* (bottom; SEQ ID NO:3). Conserved or identical residues are highlighted.

FIG. 12A shows the nucleic acid sequence of PST-16 (SEQ ID NO: 14), which encodes a self-priming poly-sialyltransferase protein. The protein is a fusion of a truncated bi-functional α-2,3/α-2,8-sialyitransferase (Cst-II protein from *C. jejuni*) and a poly-sialyltransferase (Pst from *E. coli*). The Cst-II sequence begins at the 5' end and is italicized. An amino acid linker between the two enzymes is underlined and in bold. The remaining sequence through the 3' end is the *E. coli* Pst.

FIG. 12B shows the amino acid sequence of the PST-16 self-priming poly-sialyltransferase protein (SEQ ID NO: 15). The Cst-II sequence begins at the amino terminus and is italicized. An amino acid linker between the two enzymes is underlined and in bold. The remaining sequence through the carboxy terminus is the *E. coli* Pst.

DETAILED DESCRIPTION OF THE INVENTION

I. Introduction

Figure 1:
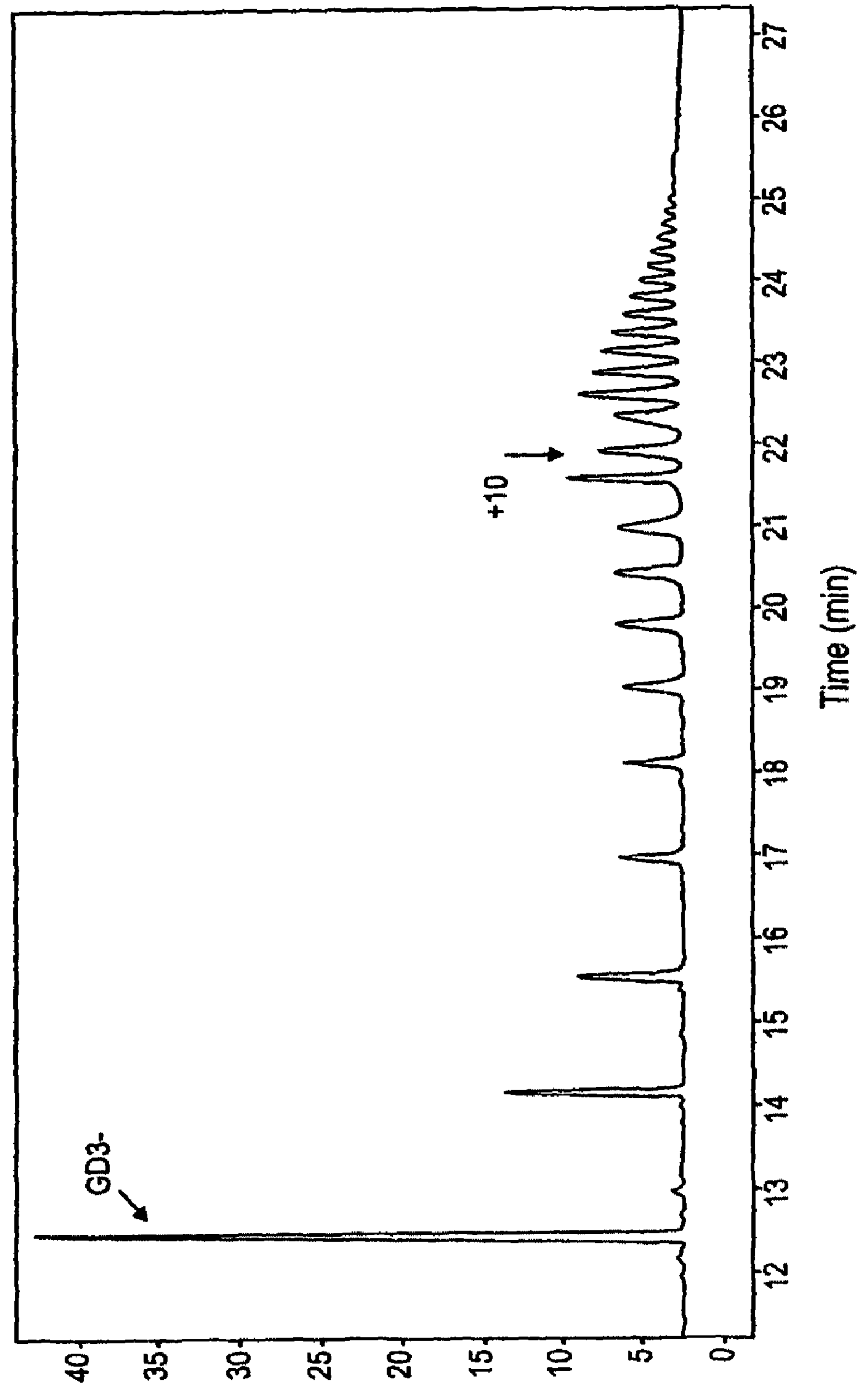
FIG. 1 provides a representative capillary electrophoresis (CE) electropherogram of a PST sialyltransferase reaction. Arrows indicate the position of the labeled GD3 acceptor and a reaction product conjugated to more than ten sialic acid residues.
Figure 2B:
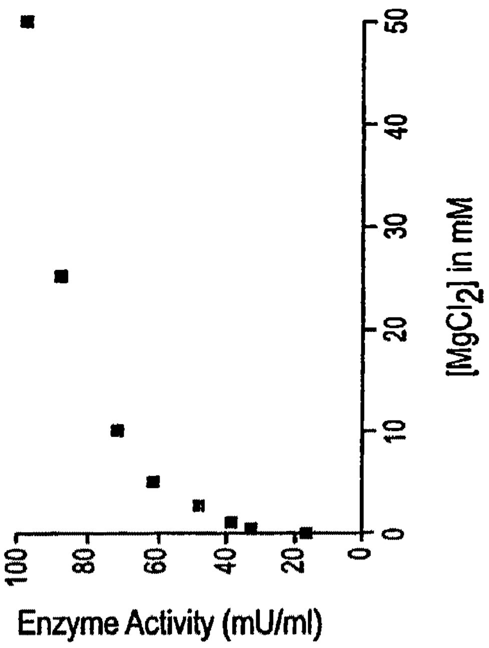
FIG. 2B shows the relationship between PST-13 enzyme activity and $MgCl_2$ concentration.
Figure 2A:
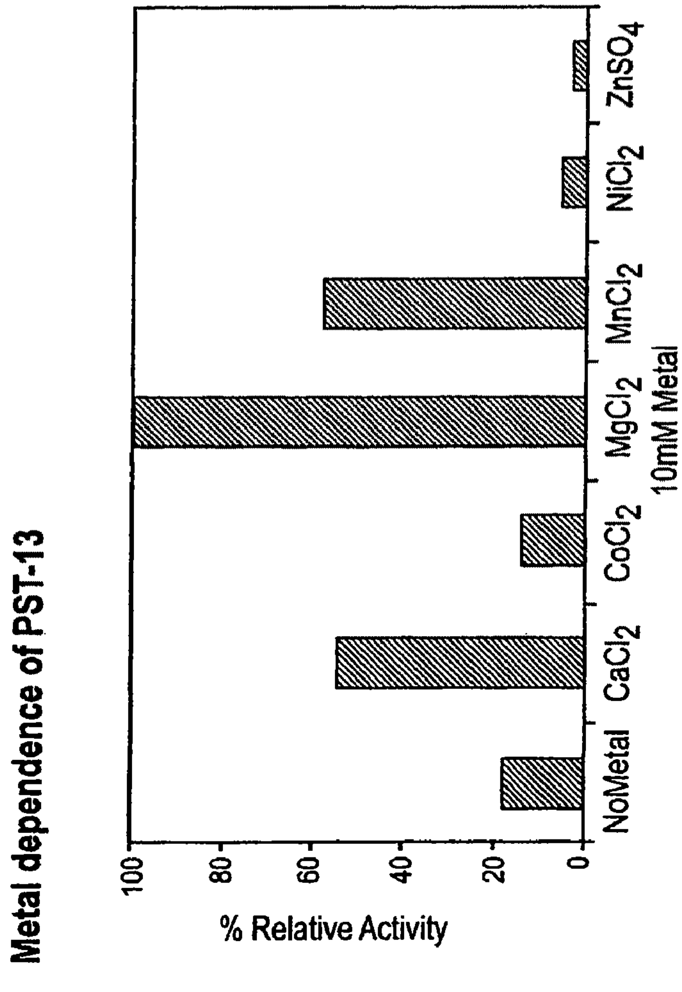
FIG. 2A shows the activity of the PST-13 protein in the presence of various divalent cations (10 mM concentrations).

A self-priming poly-sialyltransferase has been constructed to efficiently make poly-sialylated products, e.g., oligosaccharides, glycoproteins, and glycolipids mat contain poly-sialic acid groups. The self priming poly-sialyltransferase is a fusion of a bi-functional sialyitransferase and a poly-sialyltransferase. Surprisingly, both enzymes were functional when fused together. The bi-functional sialyltransferase typically adds sialic acid groups in an α-2,3/α-2,8 configuration to an acceptor molecule. The poly-sialyltransferase then conjugates additional sialic acid residues in an α-2,8 or an α-2,9 configuration.

The exemplary self-priming poly-sialyltransferase is a fusion of bacterial sialyltransferase and a bacterial poly-sialyltransferase. The fusion of bacterial enzymes is able to conjugate poly-sialic acid to a glycoprotein acceptor molecule. Unexpectedly, the fusion protein is more active than a mixture of the unfused parent enzymes.

II. Definitions

The following abbreviations are used herein:

Ara=arabinosyl;

Fru=fructosyl;

Fuc=fucosyl;

Gal=galactosyl;

GalNAc=N-acetylgalactosaminyl;

Glc=glucosyl;

GlcNAc=N-acetylglucosaminyl;

Man=mannosyl; and

NeuAc=sialyl (N-acetylneuraminyl).

An "acceptor substrate" or an "acceptor saccharide" for a glycosyltransferase, e.g., a self-priming poly-sialyltransferase protein, is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate can vary for different types of a particular glycosyltransferase. Accordingly, the term "acceptor substrate" is taken in context with the particular glycosyltransferase of interest for a particular application. Acceptor substrates for self-priming poly-sialyltransferase proteins, and additional glycosyltransferases, are described herein.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrate for self-priming poly-sialyltransferase proteins include, e.g., activated sugar nucleotides comprising the desired sialic acid. For instance, in the case of NeuAc, the activated sugar is CMP-NeuAc. Bacterial, plant, and fungal systems can sometimes use other activated nucleotide sugars.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

As used herein, a "sialic acid moiety" refers to a molecule that includes sialic acid or that can be derived from sialic acid. Sialic acid moieties are usually monosaccharides, e.g., CMP-sialic acid.

As used herein, a "self-priming poly-sialyltransferase protein" refers to a recombinant protein that is a fusion of a bi-functional sialyltransferase and a poly-sialytransferase. The self-priming poly-sialyltransferase protein is thus conjugates a first single sialic acid moiety to a non-sialic acid sugar residue in acceptor substrate through the activity of bi-functional sialyltransferase, typically in an α-2,3 configuration. The self-priming poly-sialyltransferase protein also conjugates a second single sialic acid moiety to previously added first single sialic acid moiety through the activity of bi-functional sialyltransferase, typically in an α-2,8 configuration. The self-priming poly-sialyltransferase protein can then conjugate one or more sialic acid moieties to the second single sialic acid moiety through the activity of the poly-sialyltransferase. In some embodiments, the activity of the poly-sialyltransferase produces a polymer of sialic acid moieties. Exemplary amino acid and nucleic acid sequences of a self-priming poly-sialyltransferase are found e.g., at SEQ ID NO: 1 and 2.

As used herein, a "polymer of sialic acid moieties" refers to a multitude of conjugated sialic acid moieties, i.e., more than one. Such sialic acid polymers include homo-polymers of sialic acid that are all linked in the same configuration, e.g., a "homo-polymer of α-2,8-linked sialic acid moieties" or a "homo-polymer of α-2,9-linked sialic acid moieties." Sialic acid polymers also include a "co-polymer of α-2,8/α-2,9-linked sialic acid moieties." The linkage of the sialic acid polymers will depend on the identity of the poly-sialyltransferase included in the self-priming poly-sialyltransferase protein.

As used herein, a "polysialylated product or product saccharide" refers an oligosaccharide, a polysaccharide, or a carbohydrate moiety, either unconjugated or conjugated to a glycolipid or a glycoprotein, e.g., a biomolecule, that includes at least three sialic acid moieties. In preferred embodiments of a polysialylated product or product saccharide, a first single sialic acid moiety is conjugated to an acceptor substrate or biomolecule in an α-2,3 configuration; a second single sialic acid moiety is conjugated to the first single sialic acid moiety in an α-2,8 configuration; and one or more sialic acid moieties are conjugated to the second single sialic acid moiety. A polysialylated product or product saccharide comprises at least 3 sialic acid moieties. In other embodiments, a poly-sialylated product or product saccharide comprises at least 5, 7, 12, 25, 45, 80, 100, 150, 200, 250, or 500 sialic acid moieties. In further embodiments, a polysialylated product or product saccharide comprises at least between 3 and 12, 25, 45, 80, 100, 150, 200, 250, or 500 sialic acid moieties. In still further embodiments, a polysialylated product or product saccharide comprises up to 12, 25, 45, 80, 100, 150, 200, 250, or 500 sialic acid moieties.

In some embodiments other sugar moieties, e.g., fucose, galactose, GalNAc, glucose, or GluNAc, are also added to the acceptor substrate through the action of additional glycosyltransferases to produce the poly-sialylated product saccharide. In some embodiments, the acceptor substrate comprises a galactose moiety and the self-priming poly-sialyltransferase protein is used to add a first single sialic acid moiety to the galactose moiety in an α-2,3 configuration; to add a second single sialic acid moiety in an α-2,8 configuration to the first sialic acid moiety; and to add one or more sialic acid moieties to the second single sialic acid moiety, making the poly-sialylated product saccharide. In other embodiments, the acceptor substrate comprises a first sialic acid moiety in an α-2,3 configuration and the self-priming poly-sialyltransferase protein is used to a second single sialic acid moiety in an α-2,8 configuration to the first sialic acid moiety, and to add one or more sialic acid moieties to the second single sialic acid moiety, making the poly-sialylated product saccharide. In a further embodiment, the acceptor substrate comprises a first sialic acid moiety in an α-2,3 configuration conjugated to a second single sialic acid moiety in an α-2,8 configuration to the first sialic acid moiety, and the self-priming poly-sialyltransferase protein is used to add one or more sialic acid moieties to the second single sialic acid moiety, making the poly-sialylated product saccharide.

The term "sialic acid" or "sialic acid moiety" refers to any member of a family of nine-carbon carboxylated sugars. The most common member of the sialic acid family is N-acetylneuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261:11550-11557; Kanamori et al., *J. Biol. Chem.* 265:21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2:25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

Much of the nomenclature and general laboratory procedures required in this application can be found in Sambrook, et al., *Molecular Cloning: A Laboratory Manual* (2nd Ed.), Vol. 1-3, Cold Spring Harbor Laboratory, Cold Spring Harbor, N.Y., 1989. The manual is hereinafter referred to as "Sambrook et al."

The terms "bi-functional sialyltransferase" or a nucleic acid encoding a "bi-functional sialyltransferase" refer to nucleic acids and polypeptide polymorphic variants, alleles, mutants, and interspecies homologs that: (1) have an amino acid sequence that has at least 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a bi-functional sialyltransferase nucleic acid or to an amino acid sequence of a bi-functional sialyltransferase protein (for a bi-functional sialyltransferase from *C. jejuni*, see, e.g., SEQ ID NO: 8, 9, 10, 11, 12, or 13); (2) bind to antibodies, e.g., polyclonal antibodies, raised against an immunogen comprising an amino acid sequence of a bi-functional sialyltransferase protein, and conservatively modified variants thereof; (3) specifically hybridize under stringent hybridization conditions to an anti-sense strand corresponding to a nucleic acid sequence encoding a bi-functional sialyltransferase protein, and conservatively modified variants thereof; (4) have a nucleic acid sequence that has at least 90%, preferably at least 91%, 92%, 93%, 94%, 95%, 96%, 97%, 98%, 99%, or higher nucleotide sequence identity, preferably over a region of at least about 25, 50, 100, 200, 500, 1000, or more nucleotides, to a nucleic acid that encodes a bi-functional sialyltransferase nucleic protein, e.g., SEQ ID NO:8, 9, 10, 11, 12, or 13, or a nucleic acid encoding the catalytic domain. Preferably the catalytic domain has at least 90%, preferably at least 91%, 92%, 93%, 94%, 95%, 96%, 97%, 98%, 99% amino acid identity to the bi-functional sialyltransferase catalytic domain of SEQ ID NO:8, 9, 10, 11, 12, or 13. A polynucleotide or polypeptide sequence is typically from a bacteria including, but not limited to, *Campylobacter, Haemophilus*, and *Pasteurella*. The nucleic acids and proteins of the invention include both naturally occurring or recombinant molecules. A bi-functional sialyltransferase protein typically has α-2,3/α-2,8 sialyltransferase activity. α-2,3/α-2,8 sialyltransferase assays can be performed according to methods known to those of skill in the art, using appropriate donor substrates and acceptor substrates, as described herein.

The terms "poly-sialyltransferase" or a nucleic acid encoding "poly-sialyltransferase" refer to nucleic acids and polypeptide polymorphic variants, alleles, mutants, and interspecies homologs that: (1) have an amino acid sequence that has at least 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a poly-sialyltransferase nucleic acid or to an amino acid sequence of a poly-sialyltransferase protein (for exemplary poly-sialyltransferase protein sequences, see, e.g., SEQ ID NO:3, 4, 5, 6, and 7); (2) bind to antibodies, e.g., polyclonal antibodies, raised against an immunogen comprising an amino acid sequence of a poly-sialyltransferase protein, and conservatively modified variants thereof; (3) specifically hybridize under stringent hybridization conditions to an anti-sense strand corresponding to a nucleic acid sequence encoding a poly-sialyltransferase protein, and conservatively modified variants thereof; (4) have a nucleic acid sequence that has at least 90%, preferably at least 91%, 92%, 93%, 94%, 95%, 96%, 97%, 98%, 99%, or higher nucleotide sequence identity, preferably over a region of at least about 25, 50, 100, 200, 500, 1000, or more nucleotides, to a nucleic acid that encodes a poly-sialyltransferase, e.g., SEQ ID NO:3, 4, 5, 6, or 7, or a nucleic acid encoding the catalytic domain. Preferably the catalytic domain has at least 90%, preferably at least 91%, 92%, 93%, 94%, 95%, 96%, 97%, 98%, 99% amino acid identity to a poly-sialyltransferase catalytic domain of, e.g., SEQ ID NO: 3, 4, 5, 6, or 7. A polynucleotide or polypeptide sequence is typically from a bacteria including, but not limited to, *Campylobacter, Haemophilus*, and *Pasteurella*. The nucleic acids and proteins of the invention include both naturally occurring or recombinant molecules. A poly-sialyltransferase protein typically has poly-sialyltransferase activity, including e.g., activity to make α-2,8 linkages, α-2,9 linkages or α-2,8/α-2,9 linkages. Poly-sialyltransferase assays can be performed according to methods known to those of skill in the art, using appropriate donor substrates and acceptor substrates, as described herein.

"Commercial scale" refers to gram scale production of a poly-sialylated product in a single reaction. In preferred embodiments, commercial scale refers to production of greater than about 50, 75, 80, 90, 100, 125, 150, 175, or 200 grams of poly-sialylated product.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Those of skill recognize that many amino acids can be substituted for one another in a protein without affecting the function of the protein, i.e., a conservative substitution can be the basis of a conservatively modified variant of a protein such as the disclosed self priming sialyltransferase proteins or its component parts, e.g., a bi-functional sialyltransferase or poly-sialyltransferase. An incomplete list of conservative amino acid substitutions follows. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton, *Proteins* (1984)).

The cells and methods of the invention are useful for producing a poly-sialylated product, generally by transferring a sialic acid moiety from a donor substrate to an acceptor molecule. The cells and methods of the invention are also useful for producing a poly-sialylated product sugar comprising additional sugar residues, generally by transferring a additional monosaccharide or a sulfate groups from a donor substrate to an acceptor molecule. The addition generally takes place at the non-reducing end of an oligosaccharide, polysaccharide (e.g., heparin, carragenin, and the like) or a carbohydrate moiety on a glycolipid or glycoprotein, e.g., a biomolecule. Biomolecules as defined here include but are not limited to biologically significant molecules such as carbohydrates, oligosaccharides, peptides (e.g., glycopeptides), proteins (e.g., glycoproteins), and lipids (e.g., glycolipids, phospholipids, sphingolipids and gangliosides).

The recombinant proteins of the invention can be constructed and expressed as a fusion protein with a molecular "purification tag" at one end, which facilitates purification or identification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAspAspLys (SEQ ID NO: 16) or a substantially identical variant thereof. Other suitable tags are known to those of skill in the art, and include, for example, an affinity tag such as a hexahistidine peptide, which will bind to metal ions such as nickel or cobalt ions or a myc tag. Proteins comprising purification tags can be purified using a binding partner mat binds the purification tag, e.g., antibodies to the purification tag, nickel or cobalt ions or resins, and amylose, maltose, or a cyclodextrin. Purification tags also include maltose binding domains and starch binding domains. Purification of maltose binding domain proteins is known to those of skill in the art Starch binding domains are described in WO 99/15636, herein incorporated by reference. Affinity purification of a fusion protein comprising a starch binding domain using a betacylodextrin (BCD)-derivatized resin is described in WO 2005/014779, published Feb. 17, 2005, herein incorporated by reference in its entirety.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. The terms "nucleic acid", "nucleic acid sequence", and "polynucleotide" are used interchangeably herein.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide" or a "heterologous nucleic acid", as used herein, is one that originates from a source foreign to the particular host cell, or, if from the same source, is modified from its original form. Thus, a heterologous glycosyltransferase gene in a prokaryotic host cell includes a glycosyltransferase gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" refers to material that is substantially or essentially free from components which interfere with the activity of an enzyme. For cells, saccharides, nucleic acids, and polypeptides of the invention, the term "isolated" refers to material that is substantially or essentially free from components which normally accompany the material as found in its native state. Typically, isolated saccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligonucleotides, or other galactosylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215:403-410 and Altschuel et al. (1977) *Nucleic Acids Res.* 25:3389-3402, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always $>0$) and N (penalty score for mismatching residues; always $<0$). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N))> which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M $Na^+$ ion, typically about 0.01 to 1.0 M $Na^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to" or "specifically immunoreactive with", when referring to an antibody refers to a binding reaction which is determinative of the presence of the protein or other antigen in the presence of a heterogeneous population of proteins, saccharides, and other biologics. Thus, under designated immunoassay conditions, the specified antibodies bind preferentially to a particular antigen and do not bind in a significant amount to other molecules present in the sample. Specific binding to an antigen under such conditions requires an antibody that is selected for its specificity for a particular antigen. A variety of immunoassay formats can be used to select antibodies specifically immunoreactive with a particular antigen. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. In a preferred embodiment, antibodies that specifically bind to a self-priming poly-sialyltransferase protein are produced. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F $(ab)'_2$, a dimer of Fab which itself is a light chain joined to $V_H$-$C_H1$ by a disulfide bond. The F $(ab)'_2$ may be reduced under mild conditions to break the disulfide linkage in the hinge region, thereby converting the F $(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual*(1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to IgE protein, polymorphic variants, alleles, orthologs, and conservatively modified variants, or splice variants, or portions thereof, can be selected to obtain only those polyclonal antibodies that are specifically immunoreactive with IgE proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}P$, $^{125}I$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radiolabel into the peptide, and used to detect antibodies specifically reactive with the peptide).

The term "immunoassay" is an assay that uses an antibody to specifically bind an antigen. The immunoassay is characterized by the use of specific binding properties of a particular antibody to isolate, target, and/or quantify the antigen.

The term "carrier molecule" means an immunogenic molecule containing antigenic determinants recognized by T cells. A carrier molecule can be a protein or can be a lipid. A carrier protein is conjugated to a polypeptide to render the polypeptide immunogenic. Carrier proteins include keyhole limpet hemocyanin, horseshoe crab hemocyanin, and bovine serum albumin.

The term "adjuvant" means a substance that nonspecifically enhances the immune response to an antigen. Adjuvants include Freund's adjuvant, either complete or incomplete; Titermax gold adjuvant; alum; and bacterial LPS.

The term "contacting" is used herein interchangeably with the following: combined with, added to, mixed with, passed over, incubated with, flowed over, etc.

III. Self-Priming Poly-Sialyltransferase Polypeptides

The self-priming sialyltransferase polypeptides of the invention comprise an amino acid sequence of a bi-functional sialyltransferase and an amino acid sequence of a poly-sialyltransferase. The fusion of the two polypeptides can include an amino acid linker sequence between them. In preferred embodiments, the self-priming sialyltransferase polypeptides have both bi-functional sialyltransferase activity and poly-sialyltransferase activity.

The components of the self-priming poly-sialyltransferases, the bi-functional sialyltransferase and the poly-sialyltransferase can sometimes be identified by comparison to previously identified proteins with the same activity. Computer programs that compare previously unknown sequences to known sequences are freely available to those of skill. One such program is Cn3D which can be downloaded from www.ncbi.nlm.nih.gov/Structure/CN3D/cn3d.shtml. Cn3D correlates structure and sequence information: for example, a scientist can quickly find the residues in a crystal structure that correspond to known disease mutations, or conserved active site residues from a family of sequence homologs. Cn3D displays structure-structure alignments along with their structure-based sequence alignments, to emphasize what regions of a group of related proteins are most conserved in structure and sequence. Thus, using a program such as Cn3D, those of skill can identify conserved residues in an appropriate domain of a bi-functional sialyltransferase or a poly-sialyltransferase and moreover, can predict changes in amino acid residues that would likely not effect activity of the protein. In addition, using the Cn3D program, those of skill could also predict changes in amino acid residues that would be detrimental to bi-functional sialyltransferase activity or poly-sialyltransferase activity, and avoid them.

Any bi-functional sialyltransferase can be fused to poly-sialyltransferase to generate a self-priming sialyltransferase polypeptide using standard molecular biology techniques. In one embodiment a bacterial bi-functional sialyltransferase is used in the self-priming sialyltransferase polypeptide. In one embodiment a bacterial poly-sialyltransferase is used in the self-priming sialyltransferase polypeptide. In another embodiment both the bi-functional sialyltransferase and the poly-sialyltransferase are bacterial proteins. In one embodiment the bi-functional sialyltransferase is a CstII protein from *Campylobacter jejuni*. In one embodiment the poly-sialyitransferase is from *E. coli* or *Neisseria*. In a further embodiment the poly-sialyltransferase is selected from the group SEQ ID NO:3, 4, 5, 6, and 7 and the bi-functional sialyltransferase is selected from the group SEQ ID NO:8, 9, 10, 11, 12, and 13.

A. Bi-Functional Sialytransferase Polypeptides

As disclosed above, a bi-functional sialyltransferase protein has both α-2,3 and α-2,8 sialyltransferase activities. Examples of bi-functional sialytransferases are disclosed in e.g., U.S. Pat. No. 6,503,744 and U.S. Pat. No. 6,699,705, which are herein incorporated by reference for all purposes. In some embodiments, the self-priming poly-sialyltransferase proteins comprise a bi-functional sialyltransferase protein that is a member of CAZy family 42. See, e.g., Coutinho, P. M. & Henrissat, B. (1999) Carbohydrate-Active Enzymes server at URL: afmb.cnrs-mrs.fr/CAZY/. In other embodiments, the bi-functional sialyltransferase polypeptides comprise two motifs: sialyltransferase motif A, DVFRCNQFYFED/E (SEQ ID NO: 17), and conservatively modified variants of that sequence and sialyltransferase motif B, RITSGVYMC (SEQ ID NO: 18), and conservatively modified variants of that sequence. In some embodiments, the bi-functional sialyltransferase polypeptides comprise either the bi-functional sialyltransferase motif A DVFRCNQFYFED (SEQ ID NO: 19) or DVFRCNQFYFEE (SEQ ID NO:20), and bi-functional sialyltransferase motif B RITSGVYMC (SEQ ID NO:18). See, e.g., PCT/CA2005/001432, which is herein incorporated by reference for all purposes. The conserved sialyltransferase motifs were identified by analysis of multiple bacterial sialytransferases. The amino acid sequence of 18 sialytransferases were aligned, and the conserved sialyltransferase sequence motifs A and B were identified by visual inspection.

In preferred embodiments the m-functional sialyltransferase is a CstII protein from *C. jejuni*. Bi-functional sialyltransferase proteins or nucleic acids can be isolated from the following *C. jejuni* strains: OH4384, GenBank accession number AR271700; OH4382; O:10, GenBank accession number AR271701; O:23, GenBank accession number AF401529; O:41, GenBank accession number AR271702; and HB93-13, GenBank accession number AY297047. See also, e.g., U.S. Pat. No. 6,503,744 and U.S. Pat. No. 6,699,705, which are herein incorporated by reference for all purposes.

In some embodiments the bi-functional sialyltransferase polypeptides also comprise other amino acid residues that appear to be important for enzymatic activity. For example, the structure of Cst-II from *Campylobacter jejuni* strain OH4384 has been solved. (See, e.g., Chiu et al., *Nat. Struc. Mol. Biol.* 11:163-170 (2004)). Mutational analysis of the Cst-II enzyme demonstrated that, for example the arginine residue of sialyltransferase motif B is required for activity. Residues numbers are listed for the OH4384 protein; corresponding residues for other Cst-II proteins can be determined using sequence alignments. See, e.g., PCT/CA2005/001432, which is herein incorporated by reference for all purposes. The arginine residue of sialyltransferase motif B is referred to as R129 in Cst-II and correlates to R165 of the sialyltransferase consensus sequence of FIG. 1. Other amino acid residues that appear to be important for catalytic activity include Cst-II Y156, Cst-II Y162 and Cst-II H188. Other amino acids that affect protein activity are discussed in PCT/CA2005/001432.

The bi-functional sialyltransferase polypeptides can also be modified, so long as they maintain appropriate sialyltransferase activity. Modifications include truncations, described supra, and, in some embodiments, site directed mutagenesis of the protein.

Site directed mutagenesis can be used to alter the acceptor specificity of a bi-functional sialyltransferase polypeptide. Some amino acids residues that affect acceptor specificity have been identified. For example CstII enzymes from *C. jejuni* strains OH4382, OH4384, O:10, O:41, and others are all able to form α2,3 and/or α2,8 linkages. Mutation of Asn51 to a threonine residue eliminated the ability of CstII from OH4282, OH4384 to add sialic acid in an α2,8 linkage. However, mutation of Thr51 to asparagines in a mono functional O:19 strain (α2,3 linkages only), resulted in an enzyme that was able to a sialic acid in both an α2,3 as well as an α2,8 linkage. See, e.g., Gilbert et al., *J. Biol. Chem.* 277:327-337 (2002). In addition, a mutation of residue Ile53 to a glycine in CstII enzymes from *C. jejuni* strains OH4382, OH4384 resulted in large increases in enzymatic activity. Thus, mutation of this residue in a self-priming poly-sialyltransferase can be used to alter the activity of bi-functional sialyltransferase component.

B. Poly-Sialyltransferase Polypeptides

Poly-sialyltransferase proteins have previously been identified and are thus, identifiable by those of skill in the art. For example, the poly-sialyltransferases of SEQ ID NO:3, 4, 5, 6, and 7, can be aligned with the consensus sequence of pfam07388, A-2_8-polyST, Alpha-2,8-polysialyltransferase. See, e.g., Marchler-Bauer et al., *Nucleic Acids Res.* 33: D192-6 (2005). Other poly-sialyltransferase proteins that show alignment to the pfam07388 can be used in the invention. The A-2_8-polyST, Alpha-2,8-polysialyltransferase family of proteins is a group of proteins that were identified as such based on sequence comparisons. See, e.g., Steenbergen and Vimr, *J Biol Chem.* 278:15349-15359 (2003). In other embodiments, the self-priming poly-sialyltransferase proteins comprise a poly-sialyltransferase protein that is a member of CAZy family GT38. See, e.g., Coutinho, P. M. & Henrissat, B. (1999) Carbohydrate-Active Enzymes server at URL: afmb.cnrs-mrs.fr/CAZY/. Poly-sialyltransferase proteins include proteins that synthesize homo-polymers of α2,8-linked sialic acid residues, homo-polymers of α2,9-linked sialic acid residues, or co-polymers of α2,8/α2,9-linked sialic acid residues.

Exemplary polysialyltransferase proteins can be isolated from, e.g., *N. meningitides* or *E. coli* bacteria. Two such examples are shown in FIG. 11. The proteins for these poly-sialyltransferases are both from the glycosyltransferase family GT-38, which contains only bacterial members. See, e.g., Coutinho, P. M. et al., *Journal of Molecular Biology,* 328: 307-317 (2003). Although the exemplified *N. meningitides* and *E. coli* proteins make identical structures in vivo, the two protein share 33% identity, as shown in FIG. 11.

IV. Isolation of Nucleic Acids Encoding Bi-Functional Sialyltransferase Polypeptides and Poly-Sialyltransferase Polypeptides Nucleic acids that encode bi-functional sialyltransferase polypeptides or poly-sialyltransferase polypeptides include nucleic acids that encode the bi-functional sialyltransferase polypeptides or poly-sialyltransferase polypeptides described above, i.e., SEQ ID NO:3-13, and conservatively modified variants of those sequences.

Nucleic acids that encode additional bi-functional sialyltransferase polypeptides or poly-sialyltransferase polypeptides based on the information disclosed herein, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

A DNA that encodes a bi-functional sialyltransferase polypeptide or poly-sialyltransferase polypeptide, or a subsequences thereof, can be prepared by any suitable method described above, including, for example, cloning and restriction of appropriate sequences with restriction enzymes. In one preferred embodiment, nucleic acids encoding bi-functional sialyltransferase polypeptides or poly-sialyltransferase polypeptides are isolated by routine cloning methods. A nucleotide sequence encoding a bi-functional sialyltransferase polypeptide or poly-sialyltransferase polypeptide as provided in, for example, SEQ ID NO:3-13, can be used to provide probes that specifically hybridize to a gene encoding a bi-functional sialyltransferase polypeptide or poly-sialyltransferase polypeptide in a genomic DNA sample; or to an mRNA, encoding a bi-functional sialyltransferase polypeptide or poly-sialyltransferase polypeptide comprising, in a total RNA sample (e.g., in a Southern or Northern blot). Once the target nucleic acid encoding a bi-functional sialyltransferase polypeptide or poly-sialyltransferase polypeptide is identified, it can be isolated according to standard methods known to those of skill in the art (see, e.g., Sambrook et al. (1989) *Molecular Cloning: A Laboratory Manual, 2nd Ed.*, Vols. 1-3, Cold Spring Harbor Laboratory; Berger and Kimmel (1987) *Methods in Enzymology, Vol. 152: Guide to Molecular Cloning Techniques*, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length bi-functional sialyltransferase polypeptide or poly-sialyltransferase polypeptide, or subsequences thereof, e.g., containing subsequences encoding at least a subsequence of a catalytic domain of a bi-functional sialyltransferase polypeptide or poly-sialyltransferase polypeptide. These restriction enzyme fragments, encoding a bi-functional sialyltransferase polypeptide or poly-sialyltransferase polypeptide or subsequences thereof, may then be ligated, for example, to produce a nucleic acid encoding a bi-functional sialyltransferase polypeptide or poly-sialyltransferase polypeptide.

A nucleic acid encoding a bi-functional sialyltransferase polypeptide or poly-sialyltransferase polypeptide, or a subsequence thereof, can be characterized by assaying for the expressed product. Assays based on the detection of the physical, chemical, or immunological properties of the expressed protein can be used. For example, one can identify a cloned bi-functional sialyltransferase polypeptide or poly-sialyltransferase polypeptide, by the ability of a protein encoded by the nucleic acid to catalyze the transfer of a sialic acid moiety from a donor substrate to an appropriate acceptor substrate. In one method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. To assay for bi-functional sialyltransferase activity, poly-sialyltransferase activity, or self-priming poly-sialyltransferase activity, lac-FCHASE, T-ag-FCHASE, or GalNAc-Gal-NeuAc-FCHASE is used as a substrate. See, e.g., U.S. Pat. No. 6,503,744, which is herein incorporated by reference. The reaction products of other glycosyltransferases can be detected using capillary electrophoresis, e.g., to assay for a *Neisseria* IgtC enzyme, either FCHASE-AP-Lac or FCHASE-AP-Gal can be used, whereas for Hie *Neisseria* IgtB enzyme an appropriate reagent is FCHASE-AP-GlcNAc (Wakarchuk, supra). Other methods for detection of oligosaccharide reaction products include thin layer chromatography and GC/MS and are disclosed in U.S. Pat. No. 6,503,744, which is herein incorporated by reference.

Also, a nucleic acid encoding a bi-functional sialyltransferase polypeptide or poly-sialyltransferase polypeptide, or a subsequence thereof, can be chemically synthesized. Suitable methods include the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetra. Lett.,* 22:1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding bi-functional sialyltransferase polypeptides or poly-sialyltransferase polypeptides, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired bi-functional sialyltransferase polypeptide or poly-sialyltransferase polypeptide or a subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the M-functional sialyltransferase polypeptide or poly-sialyltransferase polypeptide or a protein subsequence thereof by site-directed mutagenesis. The plasmid containing the bi-functional sialyltransferase polypeptide or poly-sialyltransferase polypeptide-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202*; PCR Protocols A Guide to Methods and Applications* (Innis et al., eds) Academic Press Inc. San Diego, Calif. (1990) (Innis); Arnheim & Levinson (Oct. 1, 1990) *C&EN* 3647*; The Journal Of NIH Research* (1991) 3: 81-94; (Kwoh et al. (1989) *Proc. Natl. Acad. Sci. USA* 86:1173; Guatelli et al. (1990) *Proc. Natl. Acad. Sci. USA* 87, 1874; Lomell et al. (1989) *J. Clin. Chem.,* 35:1826; Landegren et al., (1988) *Science* 241:1077-1080; Van Brunt (1990) *Biotechnology* 8:291-294; Wu and Wallace (1989) *Gene* 4:560; and Barringer et al. (1990) *Gene* 89:117.

Some nucleic acids encoding bacterial bi-functional sialyltransferase proteins can be amplified using PCR primers based on the sequence of bi-functional sialyltransferase nucleic acids disclosed herein. Examples of PCR primers that can be used to amplify nucleic acid that encode bi-functional sialyltransferase proteins include the following primer pairs:

```
CJ-131:
                                          (SEQ ID NO: 21)
5' CTTAGGAGGTCATATGAAAAAAGTTATTATTGCTGGAATG 3'

CJ-132:
                                          (SEQ ID NO: 22)
5' CCTAGGTCGACTTATTTTCCTTTGAAATAATGCTTTATATC 3'
```

In some bacteria, nucleic acids encoding bi-functional sialyltransferase protein can be isolated by amplifying a specific chromosomal locus, e.g., the LOS locus of *C. jejuni*, and then identifying a bi-functional sialyltransferase nucleic acid typically found at that locus (see, e.g., U.S. Pat. No. 6,503,744). Examples of PCR primers that can be used to amplify an LOS locus comprising nucleic acids encoding a bi-functional sialyltransferase protein include the following primer pairs:

```
CJ42: Primer in hoptosylTase-II
                                          (SEQ ID NO: 23)
5' GC CAT TAC CGT ATC GCC TAA CCA GG 3'
25 mer

CJ43: Primer in heptosylTase-I
                                          (SEQ ID NO: 24)
5' AAA GAA TAC GAA TTT GCT AAA GAG G 3'
25 mer
```

Other physical properties of a recombinant bi-functional sialyltransferase polypeptide or poly-sialyltransferase polypeptide expressed from a particular nucleic acid, can be compared to properties of known bi-functional sialyltransferase polypeptide or poly-sialyltransferase polypeptide to provide another method of identifying suitable sequences or domains of the bi-functional sialyltransferase polypeptide or poly-sialyltransferase polypeptide that are determinants of acceptor substrate specificity and/or catalytic activity. Alternatively, a putative bi-functional sialyltransferase polypeptide or poly-sialyltransferase polypeptide can be mutated, and its role as a glycosyltransferase, or the role of particular > sequences or domains established by detecting a variation in the structure of a carbohydrate normally produced by the unmutated, naturally-occurring, or control bi-functional sialyltransferase polypeptide or poly-sialyltransferase polypeptide. Those of skill will recognize that mutation or modification of bi-functional sialyltransferase polypeptide or poly-sialyltransferase polypeptide of the invention can be facilitated by molecular biology techniques to manipulate the nucleic acids encoding the bi-functional sialyltransferase polypeptide or poly-sialyltransferase polypeptide, e.g., PCR.

Those of skill will also recognize mat nucleic acids encoding bi-functional sialyltransferase polypeptides and poly-sialyltransferase polypeptides can be joined using standard molecular biology techniques to construct a self-priming poly-sialyltransferase polypeptide. Standard assays for enzymatic activity of the bi-functional sialyltransferase polypeptide and poly-sialyltransferase polypeptide are then performed to ensure function of the fusion protein.

V. Expression of Self-Priming Poly-Sialyltransferase Polypeptides in Host Cells Self-priming poly-sialyltransferase proteins of the invention can be expressed in a variety of host cells, including *E. coli*, other bacterial hosts, and yeast The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. Candida, T. sphaerica, T. xylinus, T. famata*, and *T. versatilis*), *Debaryomyces* (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsiella, Bacillus, Pseudomonas, Proteus*, and *Salmonella.*

Once expressed in a host cell, the self-priming poly-sialyltransferase polypeptides can be used to produced poly-sialylated products. For example, the self-priming poly-sialyltransferase polypeptides can be isolated using standard protein purification techniques and used in in vitro reactions described herein to make poly-sialylated products. Partially purified self-priming poly-sialyltransferase polypeptides can also be used in in vitro reactions to make poly-sialylated products as can the permeabilized host cells. The host cells can also be used in an in vivo system (e.g., fermentative production) to produce poly-sialylated products.

Typically, the polynucleotide that encodes the self-priming poly-sialyltransferase polypeptides is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed “expression cassettes.” Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of self-priming poly-sialyltransferase polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli.*

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, N.Y.).

For expression of the self-priming poly-sialyltransferase polypeptides in yeast, convenient promoters include GAL1-10 (Johnson and Davies (1984) *Mol. Cell. Biol.* 4:1440-448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4:2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as “inducible” promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25:167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO98/20111, A construct that includes a polynucleotide of interest operably linked to gene expression control signals that, when placed in an appropriate host cell, drive expression of the polynucleotide is termed an “expression cassette.” Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and religated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kirnmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263:16297-16302.

The self-priming poly-sialyltransferase polypeptides can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the self-priming poly-sialyltransferase polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the self-priming poly-sialyltransferase polypeptides are fused to a subsequence of protein A or bovine serum albumin (BSA), for example, to facilitate purification, secretion, or stability.

The self-priming poly-sialyltransferase polypeptides of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

VI. Purification of Self-Priming Poly-Sialyltransferase Polypeptides

The self-priming poly-sialyltransferase proteins of the present invention can be expressed as intracellular proteins or as proteins that are secreted from the cell, and can be used in this form, in the methods of the present invention. For example, a crude cellular extract containing the expressed intracellular or secreted self-priming poly-sialyltransferase polypeptide can used in the methods of the present invention.

Alternatively, the self-priming poly-sialytransferase polypeptide can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol.* 182*: Guide to Protein Purification.*, Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification of the self-priming poly-sialyltransferase polypeptides of the invention, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the self-printing poly-sialyltransferase polypeptide of the invention, and corresponding detection systems are known to those of skill in the art, and several are commercially available (e.g., FLAG® (Kodak, Rochester N.Y.). Another example of a suitable tag is a polyhistidine sequence, which is capable of binding to metal chelate affinity ligands. Typically, six adjacent histidines (SEQ ID NO:25) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)). Other purification or epitope tags include, e.g., AU1, AU5, DDDDK (SEQ ID NO:26) (EC5), E tag, E2 tag, Glu-Glu, a 6 residue peptide, EYMPME (SEQ ID NO:27), derived from the Polyoma middle T protein, HA, HSV, IRS, KT3, S tage, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl laboratories, Inc.; Abeam Ltd.; and Novus Biologicals, Inc.

Purification tags also include maltose binding domains and starch binding domains. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, *E. coli* thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from *E. coli* and SBD (starch binding domain) from an amylase of *A. niger*, are described in WO 99/15636, herein incorporated by reference. Affinity purification of a fusion protein comprising a starch binding domain using a betacyclodextrin (BCD)-derivatized resin is described in WO 2005/014779, published Feb. 17, 2005, herein incorporated by reference in its entirety. In some embodiments, a self-priming poly-sialyltransferase polypeptide comprises more than one purification or epitope tag.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the self-priming poly-sialyltransferase polypeptide without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

VII. Donor Substrates and Acceptor Substrates

Suitable donor substrates used by the self-priming poly-sialyltransferase polypeptides and other glycosyltransferases in the methods of the invention include, but are not limited to, UDP-Glc, UDP-GlcNAc, UDP-Gal, UDP-GalNAc, GDP-Man, GDP-Fuc, UDP-GlcUA, and CMP-sialic acid and other activated sialic acid moieties. Guo et al., *Applied Biochem. and Biotech.* 68:1-20 (1997)

Typically, acceptor substrates include e.g., a terminal galactose for addition of a sialic acid moiety in an α-2,3 linkage, a terminal sialic acid in an α-2,3 linkage for addition of a second sialic acid in an α-2,8 linkage, or a terminal sialic acid in an α-2,8 linkage for addition of one or more sialic acid moieties in an α-2,8 linkage. Examples of suitable acceptors include a terminal Gal that is linked to GlcNAc or Glc by a β1,4 linkage, and a terminal Gal that is β1,3-linked to either GlcNAc or GalNAc. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art. The terminal residue to which the galactose moiety is attached can itself be attached to, for example, H, a saccharide, oligosaccharide, or an aglycone group having at least one carbohydrate atom. In some embodiments, the acceptor residue is a portion of an oligosaccharide that is attached to a peptide, a protein, a lipid, or a proteoglycan, for example.

Suitable acceptor substrates used by the self-priming poly-sialyltransferase polypeptides and methods of the invention include, but are not limited to, polysaccharides and oligosaccharides. The self-priming poly-sialyltransferase polypeptides described herein can also be used in multienzyme systems to produce a desired product from a convenient starting material.

Suitable acceptor substrates used by the self-priming poly-sialyltransferase polypeptides and methods of the invention include, but are not limited to, proteins, lipids, gangliosides and other biological structures (e.g., whole cells) that can be modified by the methods of the invention. These acceptor substrates will typically comprise the polysaccharide or oligosaccharide molecules described above.

The present invention provides self-priming poly-sialyltransferase polypeptides that are selected for their ability to produce oligosaccharides, glycoproteins and glycolipids having desired oligosaccharide moieties. Similarly, if present, accessory enzymes are chosen based on an desired activated sugar substrate or on a sugar found on the product oligosaccharide.

For synthesis of glycoproteins, one can readily identify suitable self-priming poly-sialyltransferase polypeptides by reacting various amounts of a self-priming poly-sialyltransferase polypeptide of interest (e.g., 0.01-100 mU/mg protein) with a glycoprotein (e.g., at 1-10 mg/ml) to which is linked an oligosaccharide that has a potential acceptor site for glycosylation by the self-priming poly-sialyltransferase protein of interest. The abilities of the recombinant self-priming poly-sialyltransferase proteins of the present invention to add a sugar residue at the desired acceptor site are compared, and a self-priming poly-sialyltransferase polypeptide having the desired property (e.g., acceptor substrate specificity or catalytic activity) is selected.

In general, the efficacy of the enzymatic synthesis of poly-sialylated oligosaccharides, glycoproteins, and glycolipids can be enhanced through use of recombinantly produced self-priming poly-sialyltransferase polypeptides of the present invention. Recombinant techniques enable production of the recombinant self-priming poly-sialyltransferase polypeptides in the large amounts that are required for large-scale in vitro oligosaccharide, glycoprotein and glycolipid modification.

In some embodiments, suitable oligosaccharides, glycoproteins, and glycolipids for use by the self-priming poly-sialyltransferase polypeptides and methods of the invention can be glycoproteins and glycolipids immobilized on a solid support during the glycosylation reaction. The term "solid support" also encompasses semi-solid supports. Preferably, the target glycoprotein or glycolipid is reversibly immobilized so that the respective glycoprotein or glycolipid can be released after the glycosylation reaction is completed. Many suitable matrices are known to those of skill in the art. Ion exchange, for example, can be employed to temporarily immobilize a glycoprotein or glycolipid on an appropriate resin while the glycosylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof, one can use protein A or G as the affinity resin. Dyes and other molecules that specifically bind to a glycoprotein or glycolipid of interest are also suitable.

Preferably, when the acceptor saccharide is a truncated version of the full-length glycoprotein, it preferably includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

VIII. Production of Poly-Sialylated Products

Self-priming poly-sialyltransferase polypeptides can be used to make poly-sialylated products in in vitro reactions mixes or by in vivo reactions, e.g., by fermentative growth of recombinant microorganisms that comprise nucleotides that encode self-priming poly-sialyltransferase polypeptides.

A. In Vitro Reactions

The self-priming poly-sialyltransferase polypeptides can be used to make poly-sialylated products in in vitro reactions mixes. The in vitro reaction mixtures can include permeabilized microorganisms comprising the self-priming poly-sialyltransferase polypeptides, partially purified self-priming poly-sialyltransferase polypeptides, or purified self-priming poly-sialyltransferase polypeptides; as well as donor substrates acceptor substrates, and appropriate reaction buffers. For in vitro reactions, the recombinant glycosyltransferase proteins, such as self-priming poly-sialyltransferase polypeptides, acceptor substrates, donor substrates and other reaction mixture ingredients are combined by admixture in an aqueous reaction medium. Additional glycosyltransferases can be used in combination with the self-priming poly-sialyltransferase polypeptides, depending on the desired poly-sialylated product. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glycosyltransferase used. For self-priming poly-sialyltransferase polypeptides, the pH range is preferably maintained from about 5.5 to 8.0.

Enzyme amounts or concentrations are expressed in activity units, which is a measure of the initial rate of catalysis. One activity unit catalyzes the formation of 1 μmol of product per minute at a given temperature (typically 37° C.) and pH value (typically 7.5). Thus, 10 units of an enzyme is a catalytic amount of that enzyme where 10 μmol of substrate are converted to 10 μmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of polysialylated product. For large-scale preparations, the reaction will often be allowed to proceed for between about 0.5-240 hours, and more typically between about 1-36 hours.

B. In Vivo Reactions

The self-priming poly-sialyltransferase polypeptides can be used to make poly-sialylated products by in vivo reactions, e.g., fermentative growth of recombinant microorganisms comprising the self-priming poly-sialyltransferase polypeptides. Fermentative growth of recombinant microorganisms can occur in the presence of medium that includes an acceptor substrate and a donor substrate or a precursor to a donor substrate, e.g., galactose or GalNAc. See, e.g., Priem et al., *Glycobiology* 12:235-240 (2002). The microorganism takes up the acceptor substrate and the donor substrate or the precursor to a donor substrate and the addition of the donor substrate to the acceptor substrate takes place in the living cell. The microorganism can be altered to facilitate uptake of the acceptor substrate, e.g., by expressing a sugar transport protein. For example, where lactose is the acceptor saccharide, *E. coli* cells that express the LacY permease can be used. Other methods can be used to decrease breakdown of an acceptor saccharide or to increase production of a donor saccharide or a precursor of the donor saccharide. In some embodiments, production of poly-sialylated products is enhanced by manipulation of the host microorganism. For example, in *E. coli*, break down of sialic acid can be minimized by using a host strain that is lack CMP-sialate synthase (NanA-). (In *E. coli*, CMP-sialate synthase appears to be a catabolic enzyme.) Also in *E. coli*, when lactose is, for example, the acceptor saccharide or an intermediate in synthesizing the poly-sialylated product, lactose breakdown can be minimized by using host cells that are LacZ-. Methods for in vivo synthesis of oligosaccharides, including oligosaccharides containing sialic acid are found in, e.g., Samain and Priem WO/2001/004341 (2001) and Johnson et al. WO/2006/034225 (2006).

C. Characterization of and Isolation of Poly-Sialylated Products

The production of poly-sialylated products can be monitored by e.g., determining that production of the desired product has occurred or by determining that a substrate such as the acceptor substrate has been depleted. Those of skill will recognize that poly-sialylated products such as oligosaccharide, can be identified using techniques such as chromatography, e.g., using paper or TLC plates, or by mass spectrometry, e.g., MALDI-TOF spectrometry, or by NMR spectroscopy. Methods of identification of poly-sialylated products are known to those of skill in the art and are found, e.g., in U.S. Pat. No. 6,699,705, which is herein incorporated by reference for all purposes and in Varki et al., *Preparation and Analysis of Glycoconjugates*, in Current Protocols in Molecular Biology, Chapter 17 (Ausubel et al. eds, 1993).

In some embodiments, the self-priming poly-sialyltransferase polypeptides and methods of the present invention are used to enzymatically synthesize a glycoprotein or glycolipid that has a substantially uniform glycosylation pattern. The glycoproteins and glycolipids include a saccharide or oligosaccharide that is attached to a protein, glycoprotein, lipid, or glycolipid for which a glycoform alteration is desired. The saccharide or oligosaccharide includes a structure that can function as an acceptor substrate for a glycosyltransferase. When the acceptor substrate is glycosylated, the desired oligosaccharide moiety is formed. The desired oligosaccharide moiety is one that imparts the desired biological activity upon the glycoprotein or glycolipid to which it is attached. In the compositions of the invention, the preselected saccharide residue is linked to at least about 30% of the potential acceptor sites of interest. More preferably, the preselected saccharide residue is linked to at least about 50% of the potential acceptor substrates of interest, and still more preferably to at least 70% of the potential acceptor substrates of interest. In situations in which the starting glycoprotein or glycolipid exhibits heterogeneity in the oligosaccharide moiety of interest (e.g., some of the oligosaccharides on the starting glycoprotein or glycolipid already have the preselected saccharide residue attached to the acceptor substrate of interest), the recited percentages include such pre-attached saccharide residues.

The term "altered" refers to the glycoprotein or glycolipid of interest having a glycosylation pattern that, after application of the self-priming poly-sialyltransferase polypeptides and methods of the invention, is different from that observed on the glycoprotein as originally produced. An example of such glycoconjugates are glycoproteins in which the glycoforms of the glycoproteins are different from those found on the glycoprotein when it is produced by cells of the organism to which the glycoprotein is native. Also provided are self-priming poly-sialyltransferase polypeptides and methods of using such proteins for enzymatically synthesizing glycoproteins and glycolipids in which the glycosylation pattern of these glycoconjugates are modified compared to the glycosylation pattern of the glycoconjugates as originally produced by a host cell, which can be of the same or a different species than the cells from which the native glycoconjugates are produced.

One can assess differences in glycosylation patterns not only by structural analysis of the glycoproteins and glycolipids, but also by comparison of one or more biological activities of the glycoconjugates. For example, a glycoprotein having an "altered glycoform" includes one that exhibits an improvement in one more biological activities of the glycoprotein after the glycosylation reaction compared to the unmodified glycoprotein. For example, an altered glycoconjugate includes one that, after application of the self-priming poly-sialyltransferase polypeptides and methods of the invention, exhibits a greater binding affinity for a ligand or receptor of interest, a greater therapeutic half-life, reduced antigenicity, and targeting to specific tissues. The amount of improvement observed is preferably statistically significant, and is more preferably at least about a 25% improvement, and still more preferably is at least about 30%, 40%, 50%, 60%, 70%, and even still more preferably is at least 80%, 90%, or 95%.

The products produced using self-priming poly-sialyltransferase polypeptides can be used without purification. However, standard, well known techniques, for example, thin or thick layer chromatography, ion exchange chromatography, or membrane filtration can be used for recovery of glycosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 Daltons can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All citations are incorporated herein by reference.

EXAMPLES

Example 1

Analysis of Poly-Sialyltransferases from *N. Meningitides* and *E. Coli*

Cloning of PST nucleic acids in expression vectors. Polysialyltransferase (PST) nucleic acids were isolated from *E. coli* and *N. meningitides*. All DNA isolations, restriction enzyme digestions, ligations, and transformations were performed as recommended by the supplier. Enzymes were obtained from New England Biolabs (Mississauga, ON). Genomic DNA was isolated using a DNeasy Tissue kit (Qiagen Inc., Mississauga, Ontario). PCR was performed using Phusion polymerase and the program: 94° C. for 5 min, 30 cycles of 94° C. for 30 sec, 55° C. for 30 sec and 72° C. for 60 sec, and finally 72° C. for 10 min Primers for the *E. coli* PST were as follows:

```
                                    (SEQ ID NO: 28)
5'-AAGGTATAAGACATATGATATTTGATGCTAGTTTAAAGAAG
and

                                    (SEQ ID NO: 29)
3'-CCTAGGTCGACTTACTCCCCCAAGAAAATCCTTTTATCGTGC.
```

The *N. meningitidis* PST was amplified in two stages to remove an internal NdeI site (T474C). Two separate PCR reactions were performed to generate two overlapping gene fragments that both contained the silent mutation due to either the 5' or the 3' primers. The two PCR products were then used with primers

```
                                    (SEQ ID NO: 30)
5'-GCTGGAGCTGGACATATGCTAAAGAAAATAAAAAAAGCTCTTTTTCA
and

                                    (SEQ ID NO: 31)
3'-GCTGGAGCTGGAGTCGACCTATTATCTATCTCTACCAATTCTATTGT
C
to amplif
```

the fun-length gene containing the silent mutation.

DNA was purified using either Qiaquick or Minelute kits from Qiagen Inc (Mississauga, Ontario). Genes digested with NdeI and SalI were ligated into pCW or pCWmalE-thrombin and men used to transform *E. coli* AD202 by electroporation. Plasmids were isolated using High Pure Plasmid Isolation kit (Roche Diagnostics, Laval, Quebec). DNA sequencing was performed using an Applied Biosystems (Montreal, Quebec) model 3100 automated DNA sequencer and the manufacturer's cycle sequencing lot N-terminal fusions to the maltose binding protein of *E. coli* included an added thrombin recognition sequence at the 3' end.

For production of PST proteins, Cells grown in the presence of IPTG were lysed with an Avestin C5 Emulsiflex cell disrupter (Avestin Ottawa, Ontario) and centrifuged at 1000×g to pellet unbroken cells. MalE-PST fusions were purified using amylose resin as described by the manufacturer (New England Biolabs, Mississauga ON).

Measurement of sialyltransferase activity—Basic assays were performed at 37° C. in 10-40 μL volumes containing 50 mM NaHEPES pH 7.5, 10 mM $MgCl_2$, 0.1-50 mM CMP-NeuAc, 0.01-5 mM labelled acceptor and various amounts of enzyme. Buffer optimization assays were done with the following buffers: 20 mM citrate-phosphate pH 6.0-8.0, 50 mM $Na_2PO_4$ pH 6.5-7.5, 50 mM NaHEPES pH 6.5-8.0, 50 mM TrisHCl pH 7.5-9.0. Metal optimization assays were performed with 10 mM $CaCl_2$, $CoCl_2$, $MgCl_2$, $MnCl_2$, $NiCl_2$, or $ZnSO_4$. For the magnesium titration, endogenous $Mg^{2+}$ was removed by addition of EDTA and then dialyzed against 20 mM TrisHCl pH 7.5. Reactions were stopped man equal volume of 50% acetonitrile, 1% sodium dodecylsulphate, 10 mM EDTA. Analysis of actions was done by capillary electrophoresis as previously described. See, e.g., Wakarchuk, W. W. and Cunningham, A. M., *Methods Mol. Biol.,* 213:263-274 (2003)).

Acceptor synthesis—The GM3/GD3/GT3-FCHASE acceptors were synthesized from Lac-FCHASE on a milligram scale. See, e.g., Wakarechuk, W. W. and Cunningham, A. M., *Methods Mol. Biol.,* 213:263-274 (2003)). CST-II was purified essentially as described by Blixt et al. See, e.g., (Blixt, O. et al., *Carbohydrate Research,* 340:1968-1972 (2005)). Purification was performed by reversed phase HPLC on a Hamiton PRP-1 10×300 mm reversed phase column using a gradient made from 10 mM ammonium acetate pH 5.5 and 100% acetonitrile. Fractions were recycled to improve purity.

Glyco-peptide acceptors, $NH_2$-VGVT[GalNAc-α-]ETP-COOH (SEQ ID NO:32), were obtained from Sussex Research Laboratories (Ottawa, Canada) and then N-terminally labelled with FCHASE as described for the amino-phenyl glycosides. β-1,3-linked galactose was added to produce the T-antigen structure. Sialic acid was added to the O-linked structure Gal-β-1,3-GalNAc-α-Thr using Cst-I and Cst-II to give mono-, di, and tri-sialylated acceptors. All peptide substrates were purified by reversed phase chromatography on the column described above.

Mass Spectrometry—After synthesis and purification the FCHASE labelled compounds were analyzed by mass spectrometry. A Prince CE system (Prince Technologies, The Netherlands) was coupled to a 4000 QTRAP mass spectrometer (Applied Biosystems/MDS Sciex, Canada). A sheath solution (isopropanol-methanol, 2:1) was delivered at a flow rate of 1.0 uL/min. Separations were obtained on about 90 cm length bare fused-silica capillary using 15 mM ammonium acetate deionized water, pH 9.0. The 5 kV of electrospray ionization voltage were used for positive ion mode detection.

Comparison of *N. meningitidis* and *E. coli* polysialyltransferases. The bacterial PST proteins were expressed by themselves and as fusion proteins with the maltose binding protein of *E. coli* (MalE) which produces a more soluble protein. (*E. coli* PST-05 and *N. meningitidis* PST-13). The enzymes can be isolated in a pellet fraction if the lysates are centrifuged at 15,000×g. With a lower speed centrifugation (3000×g) the enzyme stays in solution and can be chromatographed on the amylose resin with excellent recovery.

The activity of the individual PST enzymes was determined using the synthetic acceptors GD3-FCHASE, GT3-FCHASE, and GQ3-FCHASE (Table 1 and FIG. 1). The enzymatic synthesis of these types of acceptors has been described previously. See, e.g., Vasilu et al., *Carbohydr. Res.* 341:1447-1457 (2006). With these substrates the activity of these enzymes was shown to increase dramatically upon increasing the number of NeuAc residues from 2 to 3 (Table 2). The PST enzymes had no detectable activity when only one NeuAc residue was present In our hands the *Neisseria* enzyme is more active toward the assayed substrates than is the *E. coli* enzyme, which did not form long polymers of sialic acid data not shown). Thus, efforts focused on the *Neisseria* pst enzyme.

TABLE 1

Synthetic Acceptors

| Substrate | Structure |
|---|---|
| Lac-FCHASE | Gal-β1,4-Glc-β-FCHASE |
| T-antigen-FCHASE | Gal-β1,3-GalNAc-α-FCHASE |
| GD3-FCHASE | NeuAc-α2,8-NeuAc-α2,3-Gal-β1,4-Glc-β-FCHASE |
| GT3-FCHASE | $(NeuAc-\alpha2,8-)_2$NeuAc-α2,3-Gal-β1,4-Glc-β-FCHASE |
| GQ3-FCHASE- | $(NeuAc-\alpha2,8-)_3$NeuAc-α2,3-Gal-β1,4-Glc-β-FCHASE |

TABLE 2

| Specific activity of the MalE-PST constructs on synthetic acceptors | | |
|---|---|---|
| Enzyme | Substrate | Specific Activity (mU/mg) |
| PST-05 | GD3-FCHASE | 1178 |
| *E. coli* | GT3-FCHASE | 1694 |
| PST-13 | GD3-FCHASE | 1316 |
| *N. meningitidis* | GT3-FCHASE | 4074 |

The CE based assay used above does not permit the determination of substrate inter-conversion during the assays. Thus, apparent $K_m$ values were estimated as follows: $K_m$ for GD3-FCHASE 120 μM for PST-13, and 145 μM for PST-05; $K_m$ for CMP-NeuAc 1.4 mM for PST-13 and 3.2 mM for PST-05.

When performing assays to examine kinetic parameters, we found that PST-13 showed acceptor inhibition with higher concentrations of GD3-FCHASE. At concentrations over 2 mM the productivity of the enzyme decreased significantly (data not shown). Some degradation of the starting material was observed and was more significant at high acceptor concentrations (5 mM).

Enzymatic assays were optimized for metal and buffer composition (data not shown). The *N. meningitidis* PST enzyme showed a strong preference for $Mg^{2+}$ compared to other divalent cations. (FIG. 4A). After removing endogenous metals by dialysis with EDTA, the enzyme was titrated with $MgCl_2$ to determine the optimum concentration required for activity. *N. meningitidis* PST exhibits a four fold increase in activity with the addition of 20 mM $MgCl_2$ (FIG. 4B).

Example 2

Construction and Characterization of Self-Priming Poly-Sialytransferases

Nucleic acids that encode bifunctional α-2,3/2,8 sialytransferase (Cst-II) from *C. jejuni* were fused to nucleic acids that encode a poly-sialytransferase (Pst, siaD) from *Neisseria meningitides*. Fusions using Cst-II from *Campylobacter jejuni* strain OH4384 to PST nucleic acids are exemplified. The Cst-II OH4384 constructs includes the first 260 amino acids with the mutation I53S, which is known to stabilize the Cst-II proteins. See, e.g., Chiu, C. P. et al., *Nat. Struct. Mol. Biol.,* 11:163-170 (2004). The Cst-II OH4384 nucleic acid was amplified with primers

```
                                        (SEQ ID NO: 33)
5'-CTTAGGAGGTCATATGAAAAAAGTTATTATTGCTGGAAATG
```

which contains an NdeI site and

```
                                          (SEQ ID NO: 3
3'-GCTGGAGCTGGACATATGTCCGCCTCCAAAATTAATATTTTTTGAAA

ATTTTCC
```

which corresponds to the 3' end of cst without a stop codon, followed by a three glycine linker and an NdeI site. The pCW pst plasmids were digested with NdeI and then ligated with NdeI digested cst before transforming *E. coli* AD202 by electroporation. The orientation of the cst gene was determined with HindIII digestion and confirmed by sequencing. Three fusions were constructed: PST-17 (truncated CstII from OH4384 fused to the *Neisseria* Pst); PST-20 (truncated CstII from HS: 10 fused to the *Neisseria* Pst); and PST-21 (full length CstII from HS: 10 fused to the *Neisseria* Pst). The nucleic acid and amino acid sequences of the representative PST-17 fusion are shown in FIGS. 3A and 3B.

Figure 4:
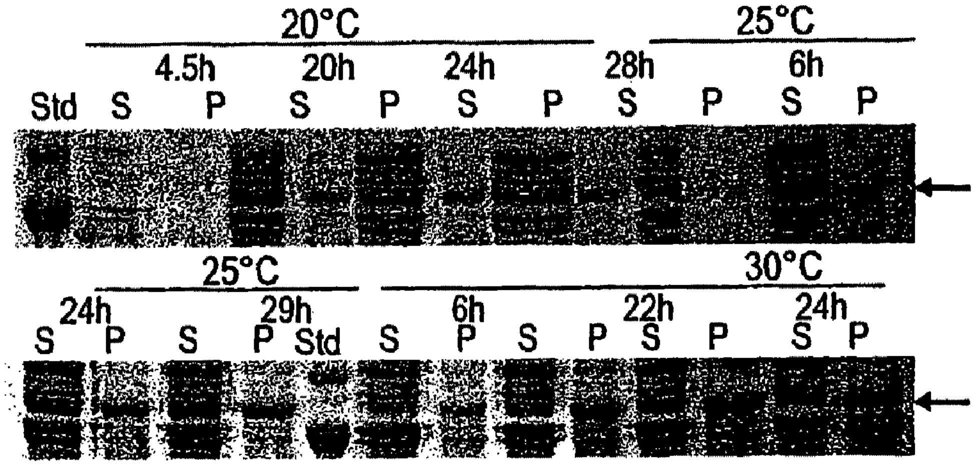
FIG. 4 shows expression levels of the PST17 self-priming poly-sialyltransferase protein in *E. coli* at different incubation times and temperatures. After harvest, cells were disrupted and centrifuged at high speed. Protein samples from the supernatant (S) and pellet (P) fractions were separated by SDS-PAGE. Gels were stained to visualize protein. The arrows indicate the position of the PST17 self-priming poly-sialyltransferase protein.

The self-priming poly-sialyltransferase proteins were expressed in *E. coli* cells and growth conditions for optimal protein expression were determined. Similar results were obtained for all three fusions; therefore, results are shown only for the PST-17 fusion. Cells were grown at 20° C., 25° C. and 30° C. for four different time periods. Aliquots of 1.5 mL were harvested, sonicated, and then centrifuged at 10,000×g for 10 mm. Results are shown in FIG. 4. Expression of the self-priming poly-sialytransferase proteins increased with time at all four temperatures.

Enzymatic activities of the self-priming poly-sialytransferase proteins were confirmed. Only the 24 hour samples of FIG. 4 were assayed Assays were done using the following reaction mixture: 0.5 mM FCHASE-Lac, 50 mM NaHEPES pH 7.5, 10 mM MgCl2, 5 mM CMP-NeuAc and 50% volume bacterial supernatant or pellet Reactions were incubated at 37° C. for 10 min and analyzed by capillary electrophoresis. Results are shown in Table 3, below. Percent GM3 is the FCHASE-GM3 found in the product In some samples, FCHASE-GD3 accumulated, suggesting mat the α-2,3 sialytransferase activity of Cst-II higher than the α-2,8 sialyltransferase of that enzyme. For example, in the PST-17 20° C. supernatant, 9% of the substrate is converted into product, but most product is FCHASE-GM3. In contrast, in the PST-21 20° C. supernatant, 7% of the substrate is converted into product with 68% FCHASE-GM3, the remaining products containing longer sialic acid polymers. Accumulations of FCHASE-GD3 were rarely observed, indicating that PST activity is high in the fusion protein. As seen in Table 3 and FIG. 4, increases protein expression levels correlated with increased activity in the sample. The highest levels of activity are shown in bold font.

TABLE 3

| ACTIVITY OF SELF-PRIMING POLY-SIALYLTRANSFERASE PROTEINS | | | | | | |
|---|---|---|---|---|---|---|
| Sample | | | Activity | [Protein] | Specific | Percent |
| ENZYME | Temp | S/P | (mU/mL) | (mg/mL) | Activity | GM3 |
| PST-17 | 20° C. | S | 5.570 | 2.112 | 2.637 | 88 |
| | | P | 3.270 | 0.365 | 8.959 | 98 |
| | 25° C. | S | 8.192 | 2.425 | 3.378 | 67 |
| | | P | 9.329 | 0.781 | 11.945 | 59 |
| | 30° C. | S | 3.976 | 2.100 | 1.893 | 58 |
| | | **P** | **13.355** | **0.877** | **15.228** | **51** |
| PST-20 | 20° C. | S | 20.329 | 2.341 | 8.684 | 99 |
| | | P | 9.278 | 0.357 | 25.989 | 90 |
| | 25° C. | S | 22.955 | 2.564 | 8.953 | 93 |
| | | P | 23.812 | 0.621 | 38.345 | 82 |
| | 30° C. | S | 8.474 | 2.037 | 4.160 | 92 |
| | | **P** | **37.167** | **0.781** | **47.589** | **79** |
| PST-21 | 20° C. | S | 14.584 | 2.187 | 6.668 | 68 |
| | | **P** | **8.267** | **0.281** | **29.420** | **86** |
| | 25° C. | S | 11.627 | 2.189 | 5.312 | 99 |
| | | P | 14.614 | 0.608 | 24.036 | 74 |
| | 30° C. | S | 7.298 | 1.803 | 4.048 | 37 |
| | | P | 14.189 | 0.905 | 15.678 | 75 |

Partial purification of the fusion proteins between CST-II and either PST was achieved by removing other proteins by binding them to a HiPrepQ FF column, followed by ammonium sulphate precipitation of the flow through fraction. Using gel densitometry we showed that PST-16 is estimated to be 6.5% of total protein and PST-17 is estimated to be 13% of total protein in this preparation. The fusion protein can also be recovered by ultracentrifugation of the flow through fraction, suggesting that the enzyme is present as a micellar preparation.

Figure 5:
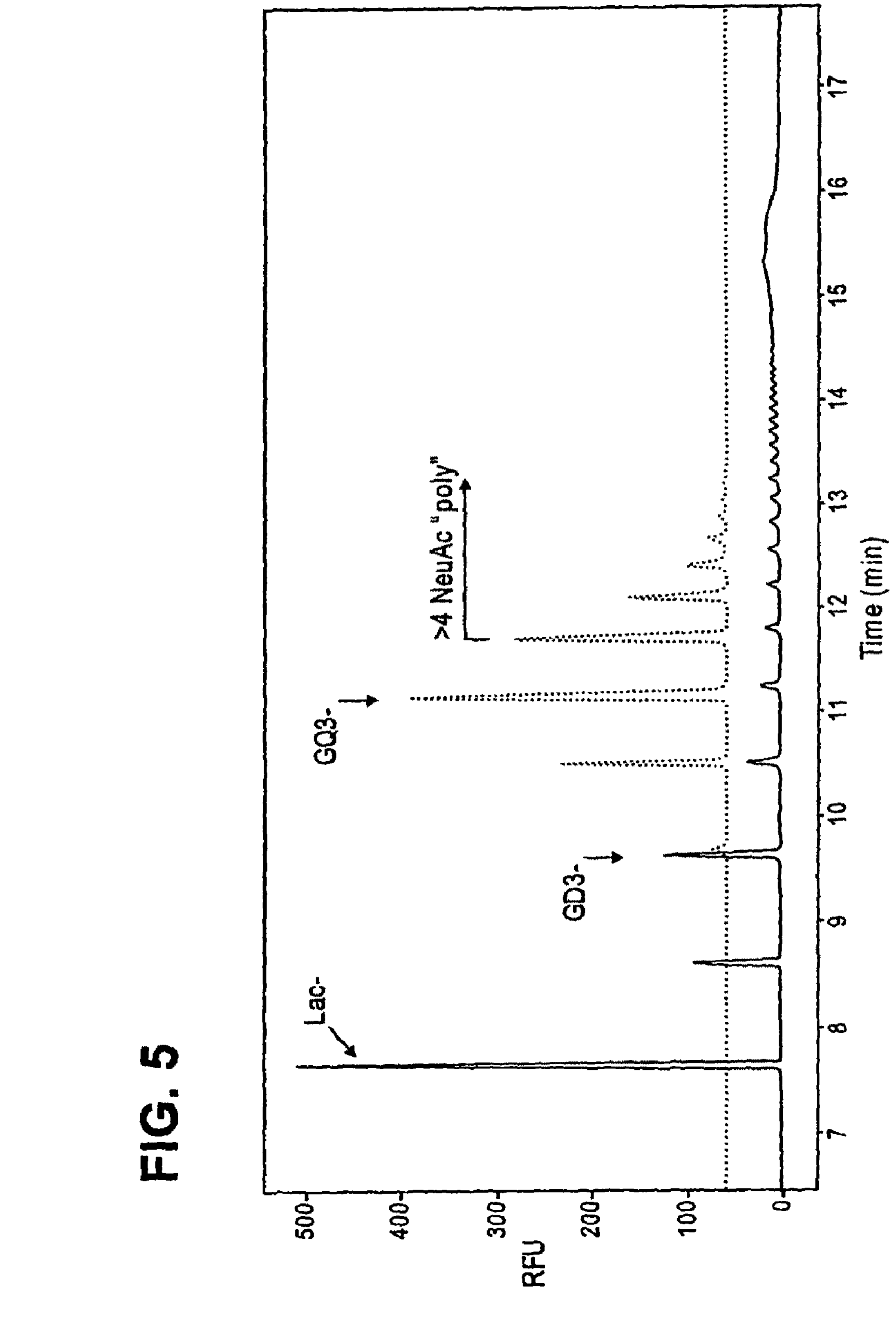
FIG. 5 shows qualitative analysis of degree of sialic acid polymerization by PST-16 and PST-17 reactions using Lac-FCHASE as an acceptor. The dotted line represents PST-16; the solid line represents PST-17. Arrows indicate the positions of Lactose (lac), GD3, GQ4, and polysialylated products conjugated to more than four sialic acid residues. The amount of polysialic acid relative to all other sialylated species (<3 sialic acid moieties) is about 50% in for each reaction.
Figures 6A, 6B, 6C, 6D:
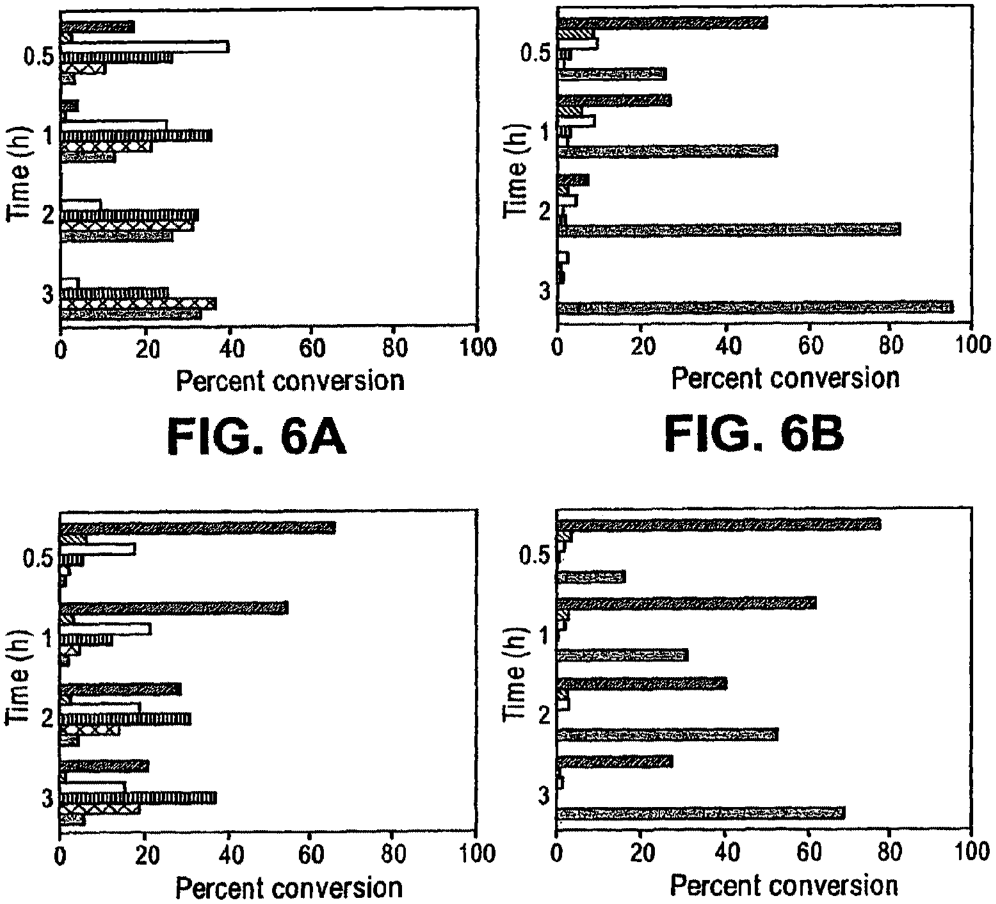
FIG. 6 shows a comparison of PST-16 and PST-17 activities on Lac- and T-Ag-FCHASE. Sialylation of the starting material: (■), +1 NeuAc; (▩), +2 NeuAc; (□), +3 NeuAc; (▥), 4 NeuAc; (▨), >4 NeuAc (■). 6A is PST-16 with Lac-FCHASE substrate. 6B is PST-17 with Lac-FCHASE substrate. 6C is PST-16 with T-Ag-FCHASE substrate. 6D is PST-17 with T-Ag-FCHASE substrate.

A fusion of Cst-II from *C. jejuni* OH4384 and the *E. coli* PST protein (PST-16) was generated and compared to the and *N. meningitidis* fusion (PST-17). Enzymatic activities of the two fusion proteins were determined and compared. Results are shown in FIGS. 5 and 6. These results show a qualitative difference in the product distribution between these CST-PST fusions. Even though the acceptor is consumed completely with PST-16, CE analysis did not detect formation of long sialic acid polymers. In contrast, with PST-17 the formation of long polymers happens from the earliest time points and in longer reactions, products greater than DP-50 can be seen. See, e.g., FIGS. 5 and 6.

Oligosaccharide acceptor substrates for self-priming poly-sialyltransferases. Two simple disaccharide acceptors, lactose and T-Ag type acceptors, were compared to determine whether the self-priming poly-sialyltransferase protein exhibited a quantitative difference in activity toward the two acceptors. The comparison was first performed on a purified sample of the unfused truncated Cst-II from *C. jejuni* strain OH4384. Assays were incubated overnight and reaction mixtures contained 300 μU enzyme, 0.5 mM substrate, 50 mM NaHEPES pH 7.5, 10 mM MgCl2, 10 mM CMP-NeuAc. Results are shown in Table 4 below. The Cst-II enzyme showed activity toward both lactose and T-Ag type acceptors, with only slight differences in product distribution detected.

TABLE 4

Activity of unfused Cst-II from OH4384 toward FCHASE-Lac or FCHASE-T-antigen acceptors

| Acceptor | Starting | +1 NeuAc | +2 NeuAc | +3 NeuAc | +4 NeuAc |
|---|---|---|---|---|---|
| FCHASE-Lac | 36.316 | 29.579 | 30.327 | 3.778 | — |
| FCHASE-T-Ag | 40.354 | 17.351 | 35.805 | 6.363 | 0.127 |

Figure 7:
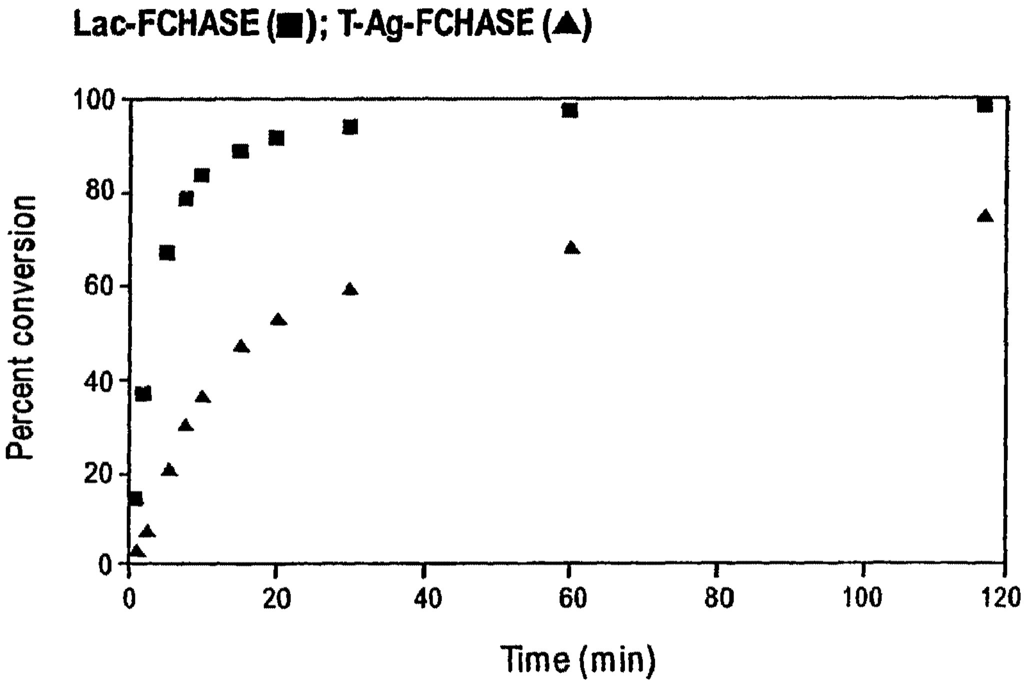
FIG. 7 shows a comparison over time of PST-17 activity on Lac-FCHASE (■) and T-Ag-FCHASE (▲).

The PST-17 enzyme made long sialic acid polymers starting from simple galactosides. A comparison of acceptors substrates was performed using Lactose, N-acetyllactosamine, and Gal-β-1,3-GalNAc-α (T-Ag) disaccharide acceptors. We observed that Lac- and LacNAc-FCHASE were equally good acceptors (data not shown), and that T-Ag-FCHASE was a slightly weaker acceptor In a time course experiment performed with a single addition of enzyme and fixed donor concentration, essentially all of the Lac-FCHASE was consumed, while 72% of the T-Ag material was consumed. See, e.g., FIG. 7.

Example 3

Glycoprotein Acceptor Substrates for Self-Priming Poly-Sialyltransferases

Figure 8:
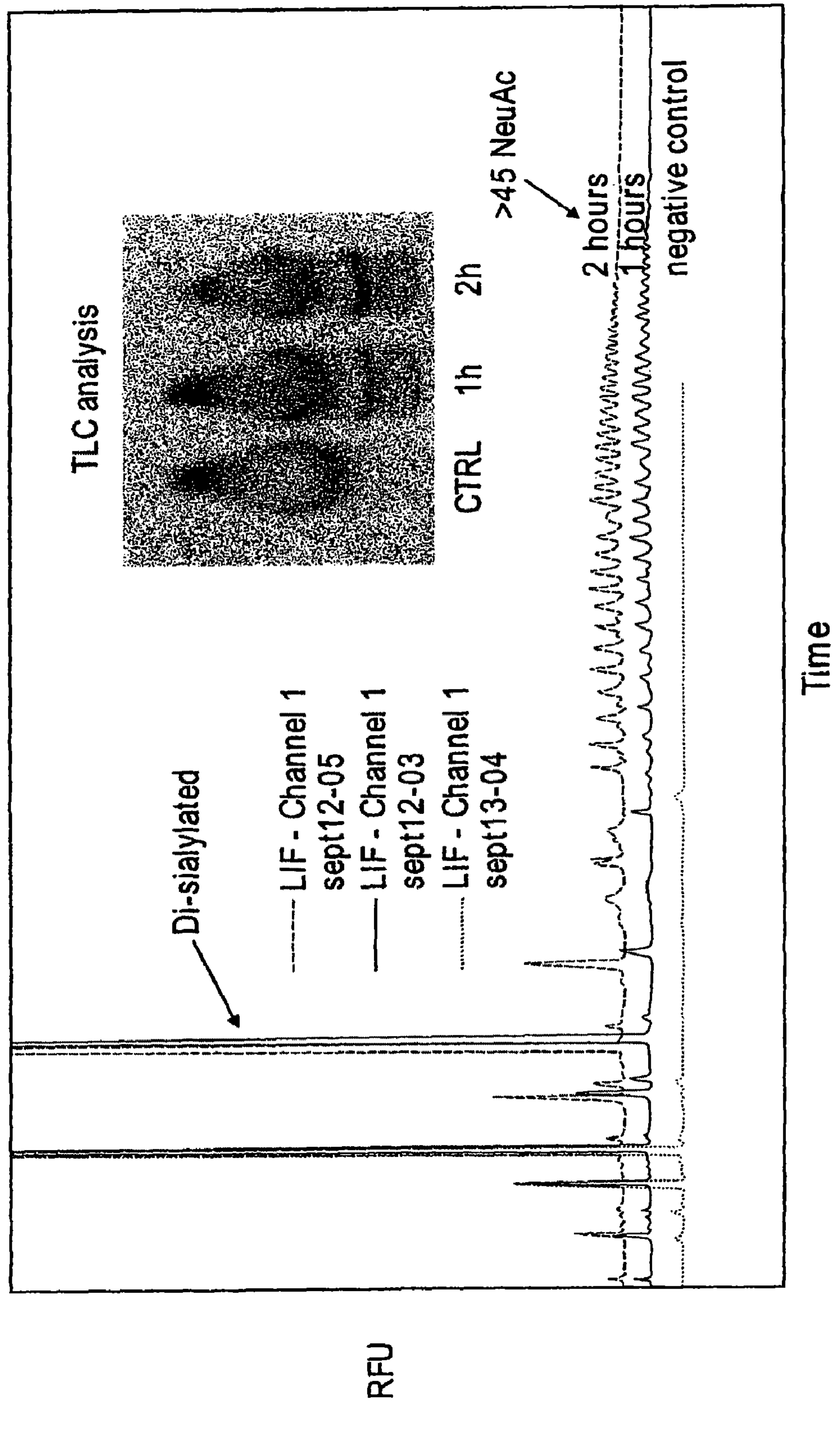
FIG. 8 shows the reaction products from conversion of glycopeptide interferon α2b-[TAg]-FCHASE to poly-sialylated products by the PST17 self-priming poly-sialyltransferase protein. The control reaction lacked CMP-sialic acid. TLC analysis is shown in the inset and shows conversion to polysialylated products at the bottom of plate. For CE analysis, the lower trace shows the negative control products, the middle trace shows the results of a one hour incubation and the upper trace shows the results of a two hour incubation. Disialylated products and products with more than 45 sialic acid residues are indicated with arrows.

The poly-sialyltransferase of PST17 was tested using a partially glycosylated IFNα2b[GalNAc-Gal-NeuAc]-FCHASE glycopeptide. Assay conditions were as follows: 50 mM NaHEPES pH 7.5, 5 mM MnCl2, 5 mM MgCl2, 5 mM CMP-NeuAc, 0.0684 mM IFNα2b[GalNAc-Gal-NeuAc]-FCHASE glycopeptide. Reactions were incubated at 37° C. for 1 hour and 2 hours. A negative control did not include CMP-NeuAc in the reaction mixture. Results of TLC and CB analysis is shown in FIG. 8. After 1 hour incubation at 37° C. there is 49.9% conversion to sialylated product and after 2 hours there is 62.5% conversion to sialylated product. CE traces in FIG. 8 clearly show that the products have multiple sialic acid residues attached. A glycopeptide acceptor was also a very good acceptor for the PST-17 fusion protein, and long PSA polymers could be seen in CE analysis of those reactions. (Data not shown.) The glyco-peptide acceptors, NH2-VGVT[GalNAc-α-]ETP-COOH (SEQ ID NO:32), were obtained from Sussex Research Laboratories (Ottawa, Canada) and then N-terminally labelled with FCHASE as described for the amino-phenyl glycosides.

Example 4

Comparison of the Fusion Protein with Mixtures of the Individual Parent Enzymes In order to evaluate whether the fusion protein functions more efficiency than the unfused parent enzymes mixed together, we performed experiments where we controlled the stoichiometry of the individual sialyltransferases. The stoichiometry of the mixtures was calculated using gel densitometry. Care was taken not to overload the gels so that the protein bands were not saturated. Gels were stained with SYPRO Orange and protein was quantitated with software provided with Imager system. Reactions contained 4 μM enzyme based on the percentage present in the separate preparations.

Figures 9A, 9B:
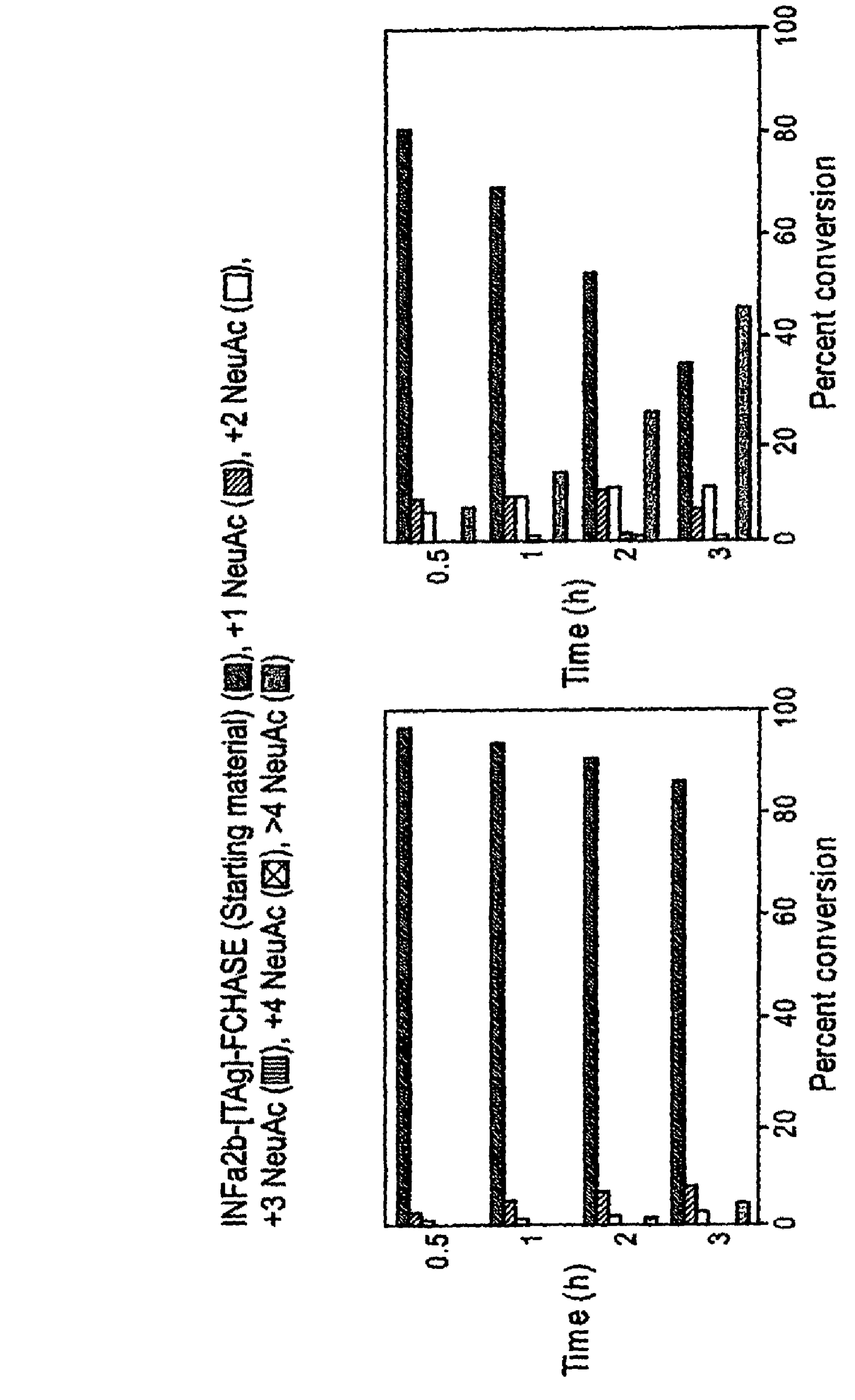
FIG. 9A is the unfused enzyme mixture: CST-81 and PST-13.
FIG. 9B is the PST-17 fusion enzyme. Figure legend: IFNα2b-[TAg]-FCHASE (Starting material) (■); +1 NeuAc (▩); +2 NeuAc (□); +3 NeuAc (▥); +4 NeuAc (▨); >4 NeuAc (■).
Figures 10A, 10B:
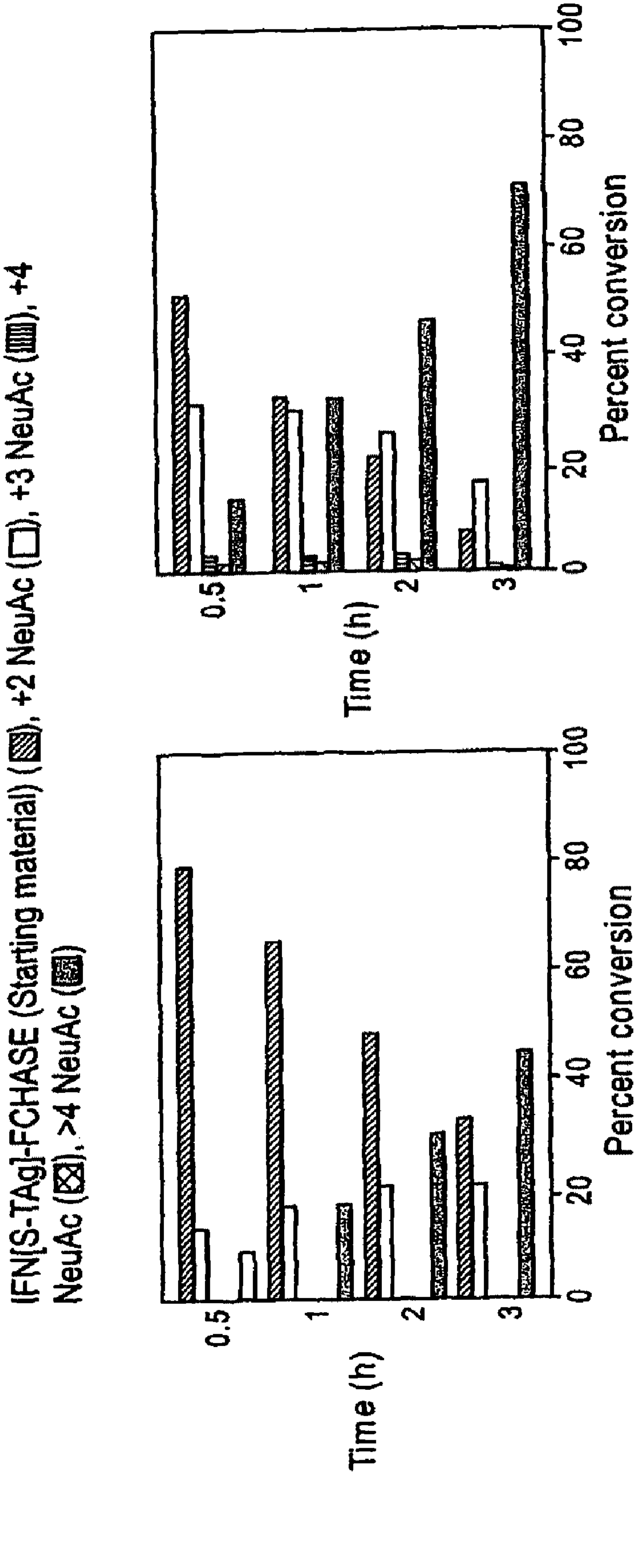
FIG. 10A is the unfused enzyme mixture: CST-81 and PST-13.
FIG. 10B is the PST-17 fusion enzyme. Figure legend: IFN[S-TAg]-FCHASE (Starting material) (▩); +2 NeuAc (□); +3 NeuAc (▥); +4 NeuAc (▨); >4 NeuAc (■).

Results are shown in FIGS. 9 and 10. The fusion protein is a more efficient catalyst making four times as much polysialic acid product on the T-Ag-containing glycopeptides (17% PSA versus 4% PSA for the combination of unfused parent enzymes). See, e.g., FIG. 9. Although less striking, similar results were obtained using a mono-sialylated T-Ag-glycopeptide (S-T-Ag-glycopeptide) acceptor also. See, e.g., FIG. 10. Significantly, reaction products from the unfused enzyme mixture consistently had much higher levels of the di-sialylated intermediate at all time points and regardless of the starting product. Moreover, at very short reaction times, the fusion protein PST-17 generates PSA material from either type of acceptor, separate enzymes do not.

Although the foregoing invention has been described in some detail by way of illustration and example for purposes of clarity of understanding, it will be readily apparent to one of ordinary skill in the art in light of the of the teachings of this invention that certain changes and modifications may be made thereto without departing from the spirit or scope of the appended claims.

What is claimed is:

1. A self-priming poly-sialyltransferase fusion protein comprising a bi-functional sialyltransferase comprising an amino acid sequence with at least 95% sequence identity to the amino acid sequence of SEQ ID NO: 8 and having α-2,3 and α-2,8 activity and a poly-sialyltransferase comprising an amino acid sequence with at least 95% sequence identity to the amino acid sequence of SEQ ID NO: 3 and having α-2,8 and/or α-2,9 activity, wherein the self-priming poly-sialyltransferase fusion protein transfers sialic acid moieties from a donor substrate to an acceptor substrate to produce a poly-sialylated product and wherein the poly-sialylated product comprises an oligosaccharide that comprises at least three sialic acid moieties.

2. The self-priming poly-sialyltransferase fusion protein of claim 1, wherein the oligosaccharide comprises at least five, nine, or twelve sialic acid moieties.

3. The self-priming poly-sialyltransferase fusion protein of claim 1, wherein the self-priming poly-sialyltransferase transfers a first sialic acid moiety to a terminal galactose on the acceptor substrate.

4. The self-priming poly-sialyltransferase fusion protein of claim 1, wherein the bi-functional sialyltransferase and the poly-sialyltransferase are bacterial proteins.

5. The self-priming poly-sialyltransferase fusion protein of claim 1, wherein the poly-sialyltransferase is from a bacterium selected from *Escherichia coli* or *Neisseria meningitidis*.

6. The self-priming poly-sialyltransferase fusion protein of claim 1, wherein the poly-sialyltransferase has the amino acid sequence of SEQ ID NO: 3 and the bi-functional sialyltransferase has the amino acid sequence of SEQ ID NO: 8.

7. The self-priming poly-sialyltransferase fusion protein of claim 1, wherein the bi-functional sialyltransferase is a *Campylobacter* protein.

8. A reaction mixture comprising the self-priming poly-sialyltransferase fusion protein of claim 1.

9. A method of producing a poly-sialylated oligosaccharide comprising:

a) contacting an acceptor substrate comprising an oligosaccharide with the self-priming poly-sialyltransferase fusion protein of claim 1, and with a donor substrate comprising a sialic acid moiety; and b) transferring at least three sialic acid moieties from the donor substrate to the acceptor substrate, thereby producing the poly-sialylated oligosaccharide.

10. The method of claim 9, wherein the poly-sialylated oligosaccharide comprises at least five, nine, or twelve sialic acid moieties.

11. The method of claim 9, wherein the acceptor substrate is a glycoprotein.

12. The method of claim 9, wherein the acceptor substrate comprises a terminal galactose.

13. The method of claim 9, wherein the method is performed at a commercial scale of production.

14. The method of claim 9, further comprising isolating the poly-sialylated oligosaccharide.

15. The self-priming poly-sialyltransferase fusion protein of claim 1, wherein said self-priming poly-sialyltransferase fusion protein comprises an amino acid linker between the bi-functional sialyltransferase and the poly-sialyltransferase.

* * * * *

SEQUENCE LISTING

<160> NUMBER OF SEQ ID NOS: 34

<210> SEQ ID NO 1
<211> LENGTH: 2283
<212> TYPE: DNA

<213> ORGANISM: Artificial Sequence
<220> FEATURE:
<223> OTHER INFORMATION: Description of Artificial Sequence:PST-17 self-priming poly-sialyltransferase fusion of truncated bi-functional alpha-2,3/alpha-2,8-sialyltransferase (C. jejuni Cst-II) and poly-sialyltransferase (N. meningitidis strain 992B Pst)

<400> SEQUENCE: 1

```
atgaaaaaag ttattattgc tggaaatgga ccaagtttaa aagaaattga ttattcaaga     60
ctaccaaatg attttgatgt atttagatgt aatcaatttt attttgaaga taaatactat    120
cttggtaaaa aatgcaaggc agtattttac aatcctagtc tttttttga acaatactac    180
actttaaaac atttaatcca aaatcaagaa tatgagaccg aactaattat gtgttctaat    240
tacaaccaag ctcatctaga aaatgaaaat tttgtaaaaa ctttttacga ttattttcct    300
gatgctcatt tgggatatga tttttcaaa caacttaaag attttaatgc ttattttaaa    360
tttcacgaaa tttatttcaa tcaaagaatt acctcagggg tctatatgtg tgcagtagcc    420
atagccctag gatacaaaga aatttatctt tcgggaattg atttttatca aaatgggtca    480
tcttatgctt ttgatactaa acaaaaaaat cttttaaaat tggctcctaa ttttaaaaat    540
gataattcac actatattgg acatagtaaa aatacagata taaaagcttt agaatttcta    600
gaaaaaactt acaaaataaa actatattgc ttatgtccta acagtctttt agcaaatttt    660
atagaactag cgccaaattt aaattcaaat tttatcatac aagaaaaaaa taactacact    720
aaagatatac tcataccttc tagtgaggct tatggaaaat tttcaaaaaa tattaatttt    780
ggaggcggac atatgctaaa gaaaataaaa aaagctcttt ttcagcctaa aaagtttttt    840
caagattcaa tgtggttgac aacatctcca ttttatctta cccccccacg taacaattta    900
tttgtcatat ctaatttagg tcagcttaac caagtccaaa gcctaattaa aatacaaaaa    960
ttaaccaata atttactagt aattttatat acttctaaaa acttaaaaat gcctaagtta   1020
gttcatcaat cagctaacaa gaatctattt gaatctattt atctatttga gcttcctaga   1080
agccctaata atataactcc taaaaaatta ctttatattt atagaagtta caaaaaaatc   1140
cttaatatta tacagcctgc tcatctctat atgctgtctt ttacaggcca ctactcctat   1200
ctgattagta ttgcaaagaa gaagaatatt acgactcatt taattgatga agggactgga   1260
acatacgctc ctttattaga atcattttca tatcatccaa caaaattaga acgtaatttg   1320
attggaaata atcttaatat taaaggatat atagatcatt ttgacatatt gcatgtcccc   1380
tttcctgaat atgctaaaaa aatatttaat gcaaaaaaat ataaccggtt ttttgcgcat   1440
gctggaggaa taagcattaa taataacatt gcaaacttac agaaaaaata tcaaatatct   1500
aaaaatgact atatttttgt tagtcaacgc taccccattt cagatgattt gtattataag   1560
agtatagtag aaatcttaaa cagcataagt ttacaaatta aaggaaagat atttattaaa   1620
ctacacccaa aagagatggg caacaactat gtaatgtctt tatttctaaa tatggtagaa   1680
ataaaccctc ggctggtagt tattaatgaa cctcctttc taattgagcc cctaatatac   1740
ttaacaaatc ctaaaggaat tataggcctg gcctctagtt ctttaattta tacaccatta   1800
ctctcaccct caacccaatg tctttctatt ggagagttaa ttattaactt aattcaaaaa   1860
tattcaatgg tggaaaacac tgaaatgatc caagaacact tagagattat taagaaattt   1920
aattttatta atatactaaa tgatttaaat ggggtaataa gtaacccccct ctttaaaaca   1980
gaagaaacat ttgaaacact tcttaaatct gcagaattcg catataaatc taaaaactac   2040
tttcaggcta ttttttactg gcaacttgcc agcaaaaaca atattacctt attagggcac   2100
```

```
aaagcattat ggtactacaa tgcactttat aatgtaaaac aaatttataa gatggaatat   2160

tcagatattt tttatatcga taatatctcc gtagactttc atagtaaaga taaattgaca   2220

tgggaaaaaa ttaaacatta ttactatttc gccgacaata gaattggtag agatagataa   2280

tag                                                                 2283


<210> SEQ ID NO 2
<211> LENGTH: 759
<212> TYPE: PRT
<213> ORGANISM: Artificial Sequence
<220> FEATURE:
<223> OTHER INFORMATION: Description of Artificial Sequence:PST-17
      self-priming poly-sialyltransferase fusion of truncated
      bi-functional alpha-2,3/alpha-2,8-sialyltransferase (C. jejuni
      Cst-II) and poly-sialyltransferase (N. meningitidis strain 992B
      Pst)

<400> SEQUENCE: 2

Met Lys Lys Val Ile Ile Ala Gly Asn Gly Pro Ser Leu Lys Glu Ile
  1               5                  10                  15

Asp Tyr Ser Arg Leu Pro Asn Asp Phe Asp Val Phe Arg Cys Asn Gln
             20                  25                  30

Phe Tyr Phe Glu Asp Lys Tyr Tyr Leu Gly Lys Lys Cys Lys Ala Val
         35                  40                  45

Phe Tyr Asn Pro Ser Leu Phe Phe Glu Gln Tyr Tyr Thr Leu Lys His
     50                  55                  60

Leu Ile Gln Asn Gln Glu Tyr Glu Thr Glu Leu Ile Met Cys Ser Asn
 65                  70                  75                  80

Tyr Asn Gln Ala His Leu Glu Asn Glu Asn Phe Val Lys Thr Phe Tyr
                 85                  90                  95

Asp Tyr Phe Pro Asp Ala His Leu Gly Tyr Asp Phe Phe Lys Gln Leu
            100                 105                 110

Lys Asp Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Gly Gly Gly His Met Leu Lys Lys Ile Lys Lys Ala
            260                 265                 270

Leu Phe Gln Pro Lys Lys Phe Phe Gln Asp Ser Met Trp Leu Thr Thr
        275                 280                 285

Ser Pro Phe Tyr Leu Thr Pro Pro Arg Asn Asn Leu Phe Val Ile Ser
    290                 295                 300

Asn Leu Gly Gln Leu Asn Gln Val Gln Ser Leu Ile Lys Ile Gln Lys
```

-continued

```
305                 310                 315                 320

Leu Thr Asn Asn Leu Leu Val Ile Leu Tyr Thr Ser Lys Asn Leu Lys
                325                 330                 335

Met Pro Lys Leu Val His Gln Ser Ala Asn Lys Asn Leu Phe Glu Ser
            340                 345                 350

Ile Tyr Leu Phe Glu Leu Pro Arg Ser Pro Asn Asn Ile Thr Pro Lys
        355                 360                 365

Lys Leu Leu Tyr Ile Tyr Arg Ser Tyr Lys Lys Ile Leu Asn Ile Ile
    370                 375                 380

Gln Pro Ala His Leu Tyr Met Leu Ser Phe Thr Gly His Tyr Ser Tyr
385                 390                 395                 400

Leu Ile Ser Ile Ala Lys Lys Lys Asn Ile Thr Thr His Leu Ile Asp
                405                 410                 415

Glu Gly Thr Gly Thr Tyr Ala Pro Leu Leu Glu Ser Phe Ser Tyr His
            420                 425                 430

Pro Thr Lys Leu Glu Arg Asn Leu Ile Gly Asn Asn Leu Asn Ile Lys
        435                 440                 445

Gly Tyr Ile Asp His Phe Asp Ile Leu His Val Pro Phe Pro Glu Tyr
    450                 455                 460

Ala Lys Lys Ile Phe Asn Ala Lys Lys Tyr Asn Arg Phe Phe Ala His
465                 470                 475                 480

Ala Gly Gly Ile Ser Ile Asn Asn Asn Ile Ala Asn Leu Gln Lys Lys
                485                 490                 495

Tyr Gln Ile Ser Lys Asn Asp Tyr Ile Phe Val Ser Gln Arg Tyr Pro
            500                 505                 510

Ile Ser Asp Asp Leu Tyr Tyr Lys Ser Ile Val Glu Ile Leu Asn Ser
        515                 520                 525

Ile Ser Leu Gln Ile Lys Gly Lys Ile Phe Ile Lys Leu His Pro Lys
    530                 535                 540

Glu Met Gly Asn Asn Tyr Val Met Ser Leu Phe Leu Asn Met Val Glu
545                 550                 555                 560

Ile Asn Pro Arg Leu Val Val Ile Asn Glu Pro Pro Phe Leu Ile Glu
                565                 570                 575

Pro Leu Ile Tyr Leu Thr Asn Pro Lys Gly Ile Ile Gly Leu Ala Ser
            580                 585                 590

Ser Ser Leu Ile Tyr Thr Pro Leu Leu Ser Pro Ser Thr Gln Cys Leu
        595                 600                 605

Ser Ile Gly Glu Leu Ile Ile Asn Leu Ile Gln Lys Tyr Ser Met Val
    610                 615                 620

Glu Asn Thr Glu Met Ile Gln Glu His Leu Glu Ile Ile Lys Lys Phe
625                 630                 635                 640

Asn Phe Ile Asn Ile Leu Asn Asp Leu Asn Gly Val Ile Ser Asn Pro
                645                 650                 655

Leu Phe Lys Thr Glu Glu Thr Phe Glu Thr Leu Leu Lys Ser Ala Glu
            660                 665                 670

Phe Ala Tyr Lys Ser Lys Asn Tyr Phe Gln Ala Ile Phe Tyr Trp Gln
        675                 680                 685

Leu Ala Ser Lys Asn Asn Ile Thr Leu Leu Gly His Lys Ala Leu Trp
    690                 695                 700

Tyr Tyr Asn Ala Leu Tyr Asn Val Lys Gln Ile Tyr Lys Met Glu Tyr
705                 710                 715                 720

Ser Asp Ile Phe Tyr Ile Asp Asn Ile Ser Val Asp Phe His Ser Lys
                725                 730                 735
```

```
Asp Lys Leu Thr Trp Glu Lys Ile Lys His Tyr Tyr Tyr Phe Ala Asp
            740                 745                 750

Asn Arg Ile Gly Arg Asp Arg
        755


<210> SEQ ID NO 3
<211> LENGTH: 495
<212> TYPE: PRT
<213> ORGANISM: Neisseria meningitidis
<220> FEATURE:
<223> OTHER INFORMATION: siaD

<400> SEQUENCE: 3

Met Leu Lys Lys Ile Lys Lys Ala Leu Phe Gln Pro Lys Lys Phe Phe
  1               5                  10                  15

Gln Asp Ser Met Trp Leu Thr Thr Ser Pro Phe Tyr Leu Thr Pro Pro
            20                  25                  30

Arg Asn Asn Leu Phe Val Ile Ser Asn Leu Gly Gln Leu Asn Gln Val
        35                  40                  45

Gln Ser Leu Ile Lys Ile Gln Lys Leu Thr Asn Asn Leu Leu Val Ile
    50                  55                  60

Leu Tyr Thr Ser Lys Asn Leu Lys Met Pro Lys Leu Val His Gln Ser
 65                  70                  75                  80

Ala Asn Lys Asn Leu Phe Glu Ser Ile Tyr Leu Phe Glu Leu Pro Arg
                85                  90                  95

Ser Pro Asn Asn Ile Thr Pro Lys Lys Leu Leu Tyr Ile Tyr Arg Ser
            100                 105                 110

Tyr Lys Lys Ile Leu Asn Ile Ile Gln Pro Ala His Leu Tyr Met Leu
        115                 120                 125

Ser Phe Thr Gly His Tyr Ser Tyr Leu Ile Ser Ile Ala Lys Lys Lys
    130                 135                 140

Asn Ile Thr Thr His Leu Ile Asp Glu Gly Thr Gly Thr Tyr Ala Pro
145                 150                 155                 160

Leu Leu Glu Ser Phe Ser Tyr His Pro Thr Lys Leu Glu Arg Tyr Leu
                165                 170                 175

Ile Gly Asn Asn Leu Asn Ile Lys Gly Tyr Ile Asp His Phe Asp Ile
            180                 185                 190

Leu His Val Pro Phe Pro Glu Tyr Ala Lys Lys Ile Phe Asn Ala Lys
        195                 200                 205

Lys Tyr Asn Arg Phe Phe Ala His Ala Gly Gly Ile Ser Ile Asn Asn
    210                 215                 220

Asn Ile Ala Asn Leu Gln Lys Lys Tyr Gln Ile Ser Lys Asn Asp Tyr
225                 230                 235                 240

Ile Phe Val Ser Gln Arg Tyr Pro Ile Ser Asp Asp Leu Tyr Tyr Lys
                245                 250                 255

Ser Ile Val Glu Ile Leu Asn Ser Ile Ser Leu Gln Ile Lys Gly Lys
            260                 265                 270

Ile Phe Ile Lys Leu His Pro Lys Glu Met Gly Asn Asn Tyr Val Met
        275                 280                 285

Ser Leu Phe Leu Asn Met Val Glu Ile Asn Pro Arg Leu Val Val Ile
    290                 295                 300

Asn Glu Pro Pro Phe Leu Ile Glu Pro Leu Ile Tyr Leu Thr Asn Pro
305                 310                 315                 320

Lys Gly Ile Ile Gly Leu Ala Ser Ser Ser Leu Ile Tyr Thr Pro Leu
                325                 330                 335

Leu Ser Pro Ser Thr Gln Cys Leu Ser Ile Gly Glu Leu Ile Ile Asn
```

```
            340                 345                 350

Leu Ile Gln Lys Tyr Ser Met Val Glu Asn Thr Glu Met Ile Gln Glu
        355                 360                 365

His Leu Glu Ile Ile Lys Lys Phe Asn Phe Ile Asn Ile Leu Asn Asp
    370                 375                 380

Leu Asn Gly Val Ile Ser Asn Pro Leu Phe Lys Thr Glu Glu Thr Phe
385                 390                 395                 400

Glu Thr Leu Leu Lys Ser Ala Glu Phe Ala Tyr Lys Ser Lys Asn Tyr
                405                 410                 415

Phe Gln Ala Ile Phe Tyr Trp Gln Leu Ala Ser Lys Asn Asn Ile Thr
            420                 425                 430

Leu Leu Gly His Lys Ala Leu Trp Tyr Tyr Asn Ala Leu Tyr Asn Val
        435                 440                 445

Lys Gln Ile Tyr Lys Met Glu Tyr Ser Asp Ile Phe Tyr Ile Asp Asn
    450                 455                 460

Ile Ser Val Asp Phe His Ser Lys Asp Lys Leu Thr Trp Glu Lys Ile
465                 470                 475                 480

Lys His Tyr Tyr Tyr Ser Ala Asp Asn Arg Ile Gly Arg Asp Arg
                485                 490                 495


<210> SEQ ID NO 4
<211> LENGTH: 492
<212> TYPE: PRT
<213> ORGANISM: Neisseria meningitidis
<220> FEATURE:
<223> OTHER INFORMATION: synE

<400> SEQUENCE: 4

Met Leu Gln Lys Ile Arg Lys Ala Leu Phe His Pro Lys Lys Phe Phe
  1               5                  10                  15

Gln Asp Ser Gln Trp Phe Ala Thr Pro Leu Phe Ser Ser Phe Ala Pro
            20                  25                  30

Lys Ser Asn Leu Phe Ile Ile Ser Thr Phe Ala Gln Leu Asn Gln Ala
        35                  40                  45

His Ser Leu Thr Lys Met Gln Lys Leu Lys Asn Asn Leu Leu Val Ile
     50                  55                  60

Leu Tyr Thr Thr Gln Asn Met Lys Met Pro Lys Leu Ile Gln Lys Ser
 65                  70                  75                  80

Val Asp Lys Glu Leu Phe Ser Val Thr Tyr Met Phe Glu Leu Pro Arg
                 85                  90                  95

Lys Pro Gly Ile Val Ser Pro Lys Lys Phe Leu Tyr Ile Gln Arg Gly
            100                 105                 110

Tyr Lys Lys Leu Leu Lys Thr Ile Gln Pro Ala His Leu Tyr Val Met
        115                 120                 125

Ser Phe Ala Gly His Tyr Ser Ser Leu Leu Ser Leu Ala Lys Lys Met
    130                 135                 140

Asn Ile Thr Thr His Leu Val Glu Glu Gly Thr Ala Thr Tyr Ala Pro
145                 150                 155                 160

Leu Leu Glu Ser Phe Thr Tyr Lys Pro Thr Lys Phe Glu Gln Arg Phe
                165                 170                 175

Val Gly Asn Asn Leu His Gln Lys Gly Tyr Phe Asp Lys Phe Asp Ile
            180                 185                 190

Leu His Val Ala Phe Pro Glu Tyr Ala Lys Lys Ile Phe Asn Ala Asn
        195                 200                 205

Glu Tyr His Arg Phe Phe Ala His Ser Gly Gly Ile Ser Thr Ser Gln
    210                 215                 220
```

Ser Ile Ala Lys Ile Gln Asp Lys Tyr Arg Ile Ser Gln Asn Asp Tyr
225 230 235 240

Ile Phe Val Ser Gln Arg Tyr Pro Val Ser Asp Glu Val Tyr Tyr Lys
245 250 255

Thr Ile Val Glu Thr Leu Asn Gln Met Ser Leu Arg Ile Glu Gly Lys
260 265 270

Ile Phe Ile Lys Leu His Pro Lys Glu Met Glu Asn Lys Asn Ile Met
275 280 285

Ser Leu Phe Leu Asn Met Val Thr Ile Asn Pro Arg Leu Val Val Ile
290 295 300

Asn Glu Pro Pro Phe Leu Ile Asp Pro Leu Ile Tyr Leu Thr Thr Pro
305 310 315 320

Lys Gly Ile Ile Gly Leu Thr Ser Thr Ser Ile Val Tyr Thr Pro Leu
325 330 335

Leu Ser Pro Thr Thr Gln Cys Leu Ser Ile Gly Gln Ile Val Ile Asp
340 345 350

Ser Ile His His Thr Ala Gln Gln Glu Asn Thr Ala Leu Ile Glu Glu
355 360 365

His Leu Glu Ile Val Lys Gln Phe Asp Phe Ile Lys Ile Leu Ser Ser
370 375 380

Ile Glu Asp Gly Ile Asp Thr Asn Ser Phe Lys Thr Glu Glu Thr Leu
385 390 395 400

Glu Met Leu Leu Lys Ser Ala Glu Tyr Ala Tyr Lys Asn Lys Asn Phe
405 410 415

Tyr Gln Ala Ile Phe Tyr Trp Gln Leu Ala Ser Asn Asn Asp Leu Ser
420 425 430

Val Leu Gly Tyr Lys Ser Leu Trp Tyr Tyr Asn Ala Leu Asn Lys Val
435 440 445

Lys Gln Asn Tyr Lys Met Lys Tyr Leu Glu Ile Asn Tyr Ile Glu Arg
450 455 460

Ile Ser Leu Tyr Phe Asn Asp Lys Asp Lys Met Ile Trp Gln Asn Ile
465 470 475 480

Lys Asn Asp Phe Phe Lys Tyr Ser Leu Cys Asn Gln
485 490

<210> SEQ ID NO 5
<211> LENGTH: 409
<212> TYPE: PRT
<213> ORGANISM: Escherichia coli
<220> FEATURE:
<223> OTHER INFORMATION: E. coli K1 neuS

<400> SEQUENCE: 5

Met Ile Phe Asp Ala Ser Leu Lys Lys Leu Arg Lys Leu Phe Val Asn
1 5 10 15

Pro Ile Gly Phe Phe Arg Asp Ser Trp Phe Phe Asn Ser Lys Asn Lys
20 25 30

Ala Glu Glu Leu Leu Ser Pro Leu Lys Ile Lys Ser Lys Asn Ile Phe
35 40 45

Ile Ile Ser Asn Leu Gly Gln Leu Lys Lys Ala Glu Ser Phe Val Gln
50 55 60

Lys Phe Ser Lys Arg Ser Asn Tyr Leu Ile Val Leu Ala Thr Glu Lys
65 70 75 80

Asn Thr Glu Met Pro Lys Ile Ile Val Glu Gln Ile Asn Asn Lys Leu
85 90 95

```
Phe Ser Ser Tyr Lys Val Leu Phe Ile Pro Thr Phe Pro Asn Val Phe
            100                 105                 110

Ser Leu Lys Lys Val Ile Trp Phe Tyr Asn Val Tyr Asn Tyr Leu Val
        115                 120                 125

Leu Asn Ser Lys Ala Lys Asp Ala Tyr Phe Met Ser Tyr Ala Gln His
    130                 135                 140

Tyr Ala Ile Phe Val Tyr Leu Phe Lys Lys Asn Asn Ile Arg Cys Ser
145                 150                 155                 160

Leu Ile Glu Glu Gly Thr Gly Thr Tyr Lys Thr Glu Lys Glu Asn Pro
                165                 170                 175

Val Val Asn Ile Asn Phe Tyr Ser Glu Ile Ile Asn Ser Ile Ile Leu
            180                 185                 190

Phe His Tyr Pro Asp Leu Lys Phe Glu Asn Val Tyr Gly Thr Tyr Pro
        195                 200                 205

Ile Leu Leu Lys Lys Lys Phe Asn Ala Gln Lys Phe Val Glu Phe Lys
    210                 215                 220

Gly Ala Pro Ser Val Lys Ser Ser Thr Arg Ile Asp Asn Val Ile His
225                 230                 235                 240

Lys Tyr Ser Ile Thr Arg Asp Asp Ile Ile Tyr Ala Asn Gln Lys Tyr
                245                 250                 255

Leu Ile Glu His Thr Leu Phe Ala Asp Ser Leu Ile Ser Ile Leu Leu
            260                 265                 270

Arg Ile Asp Lys Pro Asp Asn Ala Arg Ile Phe Ile Lys Pro His Pro
        275                 280                 285

Lys Glu Pro Lys Lys Asn Ile Asn Ala Ile Gln Lys Ala Ile Lys Lys
    290                 295                 300

Ala Lys Cys Arg Asp Ile Ile Leu Ile Thr Glu Pro Asp Phe Leu Ile
305                 310                 315                 320

Glu Pro Val Ile Lys Lys Ala Lys Ile Lys His Leu Ile Gly Leu Thr
                325                 330                 335

Ser Ser Ser Leu Val Tyr Ala Pro Leu Val Ser Lys Arg Cys Gln Ser
            340                 345                 350

Tyr Ser Ile Ala Pro Leu Met Ile Lys Leu Cys Asp Asn Asp Lys Ser
        355                 360                 365

Gln Lys Gly Ile Asn Thr Leu Arg Leu His Phe Asp Ile Leu Lys Asn
    370                 375                 380

Phe Asp Asn Val Lys Ile Leu Ser Asp Asp Ile Thr Ser Pro Ser Leu
385                 390                 395                 400

His Asp Lys Arg Ile Phe Leu Gly Glu
                405
```

<210> SEQ ID NO 6
<211> LENGTH: 409
<212> TYPE: PRT
<213> ORGANISM: Escherichia coli
<220> FEATURE:
<223> OTHER INFORMATION: E. coli K92 neuS

<400> SEQUENCE: 6

```
Met Ile Phe Asp Ala Ser Leu Lys Lys Leu Arg Lys Leu Phe Val Asn
  1               5                  10                  15

Pro Ile Gly Phe Phe Arg Asp Ser Trp Phe Phe Asn Ser Lys Asn Lys
            20                  25                  30

Ala Glu Glu Leu Leu Ser Pro Leu Lys Ile Lys Ser Lys Asn Ile Phe
         35                  40                  45

Ile Val Ala His Leu Gly Gln Leu Lys Lys Ala Glu Leu Phe Ile Gln
```

-continued

```
     50                  55                  60

Lys Phe Ser Arg Arg Ser Asn Phe Leu Ile Val Leu Ala Thr Lys Lys
 65                  70                  75                  80

Asn Thr Glu Met Pro Arg Leu Ile Leu Glu Gln Met Asn Lys Lys Leu
                 85                  90                  95

Phe Ser Ser Tyr Lys Leu Leu Phe Ile Pro Thr Glu Pro Asn Thr Phe
            100                 105                 110

Ser Leu Lys Lys Val Ile Trp Phe Tyr Asn Val Tyr Lys Tyr Ile Val
        115                 120                 125

Leu Asn Ser Lys Ala Lys Asp Ala Tyr Phe Met Ser Tyr Ala Gln His
    130                 135                 140

Tyr Ala Ile Phe Ile Trp Leu Phe Lys Lys Asn Asn Ile Arg Cys Ser
145                 150                 155                 160

Leu Ile Glu Glu Gly Thr Gly Thr Tyr Lys Thr Glu Lys Lys Lys Pro
                165                 170                 175

Leu Val Asn Ile Asn Phe Tyr Ser Trp Ile Ile Asn Ser Ile Ile Leu
            180                 185                 190

Phe His Tyr Pro Asp Leu Lys Phe Glu Asn Val Tyr Gly Thr Phe Pro
        195                 200                 205

Asn Leu Leu Lys Glu Lys Phe Asp Ala Lys Lys Ile Phe Glu Phe Lys
    210                 215                 220

Thr Ile Pro Leu Val Lys Ser Ser Thr Arg Met Asp Asn Leu Ile His
225                 230                 235                 240

Lys Tyr Arg Ile Thr Arg Asp Asp Ile Ile Tyr Val Ser Gln Arg Tyr
                245                 250                 255

Trp Ile Asp Asn Glu Leu Tyr Ala His Leu Leu Ile Ser Thr Leu Met
            260                 265                 270

Arg Ile Asp Lys Ser Asp Asn Ala Arg Val Phe Ile Lys Pro His Pro
        275                 280                 285

Lys Glu Thr Lys Lys Tyr Ile Asn Ala Ile Gln Gly Ala Ile Asn Lys
    290                 295                 300

Ala Lys Arg Arg Asp Ile Ile Ile Ile Val Glu Lys Asp Phe Leu Ile
305                 310                 315                 320

Glu Ser Ile Ile Lys Lys Cys Lys Ile Lys His Leu Ile Gly Leu Ala
                325                 330                 335

Ser Ser Ser Leu Val Tyr Ala Pro Leu Val Tyr Lys Glu Cys Lys Thr
            340                 345                 350

Tyr Ser Ile Ala Pro Ile Ile Ile Lys Leu Cys Asn Asn Glu Lys Ser
        355                 360                 365

Gln Lys Gly Ile Asn Thr Leu Arg Leu His Phe Asp Ile Leu Lys Asn
    370                 375                 380

Phe Asp Asn Val Lys Ile Leu Ser Asp Asp Ile Thr Ser Pro Ser Leu
385                 390                 395                 400

His Asp Lys Arg Ile Phe Leu Gly Glu
                405


<210> SEQ ID NO 7
<211> LENGTH: 409
<212> TYPE: PRT
<213> ORGANISM: Escherichia coli
<220> FEATURE:
<223> OTHER INFORMATION: E. coli APEC O1 orf63

<400> SEQUENCE: 7

Met Ile Phe Asp Ala Ser Leu Lys Lys Leu Arg Lys Leu Phe Val Asn
  1               5                  10                  15
```

-continued

```
Pro Ile Gly Phe Phe Arg Asp Ser Trp Phe Phe Asn Ser Lys Asn Lys
                20                  25                  30

Ala Glu Glu Leu Leu Ser Pro Leu Lys Ile Lys Ser Lys Asn Ile Phe
            35                  40                  45

Ile Ile Ser Asn Leu Gly Gln Leu Lys Lys Ala Glu Ser Phe Val Gln
        50                  55                  60

Lys Phe Ser Lys Arg Ser Asn Tyr Leu Ile Val Leu Ala Thr Glu Lys
65                  70                  75                  80

Asn Thr Glu Met Pro Lys Ile Ile Val Glu Gln Ile Asn Asn Lys Leu
                85                  90                  95

Phe Ser Ser Tyr Lys Val Leu Phe Ile Pro Thr Phe Pro Asn Val Phe
            100                 105                 110

Ser Leu Lys Lys Val Ile Trp Phe Tyr Asn Val Tyr Asn Tyr Leu Val
        115                 120                 125

Leu Asn Ser Lys Ala Lys Asp Ala Tyr Phe Met Ser Tyr Ala Gln His
    130                 135                 140

Tyr Ala Ile Phe Val Tyr Leu Phe Lys Lys Asn Asn Ile Arg Cys Ser
145                 150                 155                 160

Leu Ile Glu Glu Gly Thr Gly Thr Tyr Lys Thr Glu Lys Glu Asn Pro
                165                 170                 175

Val Val Asn Ile Asn Phe Tyr Ser Glu Ile Ile Asn Ser Ile Ile Leu
            180                 185                 190

Phe His Tyr Pro Asp Leu Lys Phe Glu Asn Val Tyr Gly Thr Tyr Pro
        195                 200                 205

Ile Leu Leu Lys Lys Lys Phe Asn Ala Gln Lys Phe Val Glu Phe Lys
    210                 215                 220

Gly Ala Pro Ser Val Lys Ser Ser Thr Arg Ile Asp Asn Val Ile His
225                 230                 235                 240

Lys Tyr Ser Ile Thr Arg Asp Asp Ile Ile Tyr Ala Asn Gln Lys Tyr
                245                 250                 255

Leu Ile Glu His Thr Leu Phe Ala Asp Ser Leu Ile Ser Ile Leu Leu
            260                 265                 270

Arg Ile Asp Lys Pro Asp Asn Ala Arg Ile Phe Ile Lys Pro His Pro
        275                 280                 285

Lys Glu Pro Lys Lys Asn Ile Asn Ala Ile Gln Lys Ala Ile Lys Lys
    290                 295                 300

Ala Lys Cys Arg Asp Ile Ile Leu Ile Thr Glu Pro Asp Phe Leu Ile
305                 310                 315                 320

Glu Pro Val Ile Lys Lys Ala Lys Ile Lys His Leu Ile Gly Leu Thr
                325                 330                 335

Ser Ser Ser Leu Val Tyr Ala Pro Leu Val Ser Lys Arg Cys Gln Ser
            340                 345                 350

Tyr Ser Ile Ala Pro Leu Met Ile Lys Leu Cys Asp Asn Asp Lys Ser
        355                 360                 365

Gln Lys Gly Ile Asn Thr Leu Arg Leu His Phe Asp Ile Leu Lys Asn
    370                 375                 380

Phe Asp Asn Val Lys Ile Leu Ser Asp Asp Ile Thr Ser Pro Ser Leu
385                 390                 395                 400

His Asp Lys Arg Ile Phe Leu Gly Glu
                405
```

<210> SEQ ID NO 8
<211> LENGTH: 291
<212> TYPE: PRT

-continued

<213> ORGANISM: Campylobacter jejuni
<220> FEATURE:
<223> OTHER INFORMATION: C. jejuni OH4384 Cst-II

<400> SEQUENCE: 8

Met Lys Lys Val Ile Ile Ala Gly Asn Gly Pro Ser Leu Lys Glu Ile
1 5 10 15

Asp Tyr Ser Arg Leu Pro Asn Asp Phe Asp Val Phe Arg Cys Asn Gln
20 25 30

Phe Tyr Phe Glu Asp Lys Tyr Tyr Leu Gly Lys Lys Cys Lys Ala Val
35 40 45

Phe Tyr Asn Pro Ile Leu Phe Phe Glu Gln Tyr Tyr Thr Leu Lys His
50 55 60

Leu Ile Gln Asn Gln Glu Tyr Glu Thr Glu Leu Ile Met Cys Ser Asn
65 70 75 80

Tyr Asn Gln Ala His Leu Glu Asn Glu Asn Phe Val Lys Thr Phe Tyr
85 90 95

Asp Tyr Phe Pro Asp Ala His Leu Gly Tyr Asp Phe Phe Lys Gln Leu
100 105 110

Lys Asp Phe Asn Ala Tyr Phe Lys Phe His Glu Ile Tyr Phe Asn Gln
115 120 125

Arg Ile Thr Ser Gly Val Tyr Met Cys Ala Val Ala Ile Ala Leu Gly
130 135 140

Tyr Lys Glu Ile Tyr Leu Ser Gly Ile Asp Phe Tyr Gln Asn Gly Ser
145 150 155 160

Ser Tyr Ala Phe Asp Thr Lys Gln Lys Asn Leu Leu Lys Leu Ala Pro
165 170 175

Asn Phe Lys Asn Asp Asn Ser His Tyr Ile Gly His Ser Lys Asn Thr
180 185 190

Asp Ile Lys Ala Leu Glu Phe Leu Glu Lys Thr Tyr Lys Ile Lys Leu
195 200 205

Tyr Cys Leu Cys Pro Asn Ser Leu Leu Ala Asn Phe Ile Glu Leu Ala
210 215 220

Pro Asn Leu Asn Ser Asn Phe Ile Ile Gln Glu Lys Asn Asn Tyr Thr
225 230 235 240

Lys Asp Ile Leu Ile Pro Ser Ser Glu Ala Tyr Gly Lys Phe Ser Lys
245 250 255

Asn Ile Asn Phe Lys Lys Ile Lys Ile Lys Glu Asn Ile Tyr Tyr Lys
260 265 270

Leu Ile Lys Asp Leu Leu Arg Leu Pro Ser Asp Ile Lys His Tyr Phe
275 280 285

Lys Gly Lys
290

<210> SEQ ID NO 9
<211> LENGTH: 291
<212> TYPE: PRT
<213> ORGANISM: Campylobacter jejuni
<220> FEATURE:
<223> OTHER INFORMATION: C. jejuni OH4382 Cst-II

<400> SEQUENCE: 9

Met Lys Lys Val Ile Ile Ala Gly Asn Gly Pro Ser Leu Lys Glu Ile
1 5 10 15

Asp Tyr Ser Arg Leu Pro Asn Asp Phe Asp Val Phe Arg Cys Asn Gln
20 25 30

Phe Tyr Phe Glu Asp Lys Tyr Tyr Leu Gly Lys Lys Cys Lys Ala Val

-continued

```
        35                  40                  45

Phe Tyr Asn Pro Ile Leu Phe Phe Glu Gln Tyr Tyr Thr Leu Lys His
     50                  55                  60

Leu Ile Gln Asn Gln Glu Tyr Glu Thr Glu Leu Ile Met Cys Ser Asn
 65                  70                  75                  80

Tyr Asn Gln Ala His Leu Glu Asn Glu Asn Phe Val Lys Thr Phe Tyr
                 85                  90                  95

Asp Tyr Phe Pro Asp Ala His Leu Gly Tyr Asp Phe Phe Lys Gln Leu
            100                 105                 110

Lys Asp Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290


<210> SEQ ID NO 10
<211> LENGTH: 291
<212> TYPE: PRT
<213> ORGANISM: Campylobacter jejuni
<220> FEATURE:
<223> OTHER INFORMATION: C. jejuni HB93-13 Cst-II

<400> SEQUENCE: 10

Met Lys Lys Val Ile Ile Ala Gly Asn Gly Pro Ser Leu Lys Glu Ile
  1               5                  10                  15

Asp Tyr Ser Arg Leu Pro Asn Asp Phe Asp Val Phe Arg Cys Asn Gln
             20                  25                  30

Phe Tyr Phe Glu Asp Lys Tyr Tyr Leu Gly Lys Lys Cys Lys Ala Val
         35                  40                  45

Phe Tyr Asn Pro Ile Leu Phe Phe Glu Gln Tyr Tyr Thr Leu Lys His
     50                  55                  60

Leu Ile Gln Asn Gln Glu Tyr Glu Thr Glu Leu Ile Met Cys Ser Asn
 65                  70                  75                  80

Tyr Asn Gln Ala His Leu Glu Asn Glu Asn Phe Val Lys Thr Phe Tyr
                 85                  90                  95

Asp Tyr Phe Pro Asp Ala His Leu Gly Tyr Asp Phe Phe Lys Gln Leu
            100                 105                 110
```

```
Lys Asp Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290


<210> SEQ ID NO 11
<211> LENGTH: 291
<212> TYPE: PRT
<213> ORGANISM: Campylobacter jejuni
<220> FEATURE:
<223> OTHER INFORMATION: C. jejuni O:10 ATCC 43438 Cst-II

<400> SEQUENCE: 11

Met Lys Lys Val Ile Ile Ser Gly Asn Gly Pro Ser Leu Lys Glu Ile
  1               5                  10                  15

Asp Tyr Ser Arg Leu Pro Asn Asp Phe Asp Val Phe Arg Cys Asn Gln
             20                  25                  30

Phe Tyr Phe Glu Asp Lys Tyr Tyr Leu Gly Lys Lys Phe Lys Ala Val
         35                  40                  45

Phe Tyr Asn Pro Gly Leu Phe Phe Glu Gln Tyr Tyr Thr Leu Lys His
     50                  55                  60

Leu Ile Gln Asn Gln Glu Tyr Glu Thr Glu Leu Ile Met Cys Ser Asn
 65                  70                  75                  80

Tyr Asn Gln Ala His Leu Glu Asn Glu Asn Phe Val Lys Thr Phe Tyr
                 85                  90                  95

Asp Tyr Phe Pro Asp Ala His Leu Gly Tyr Asp Phe Phe Lys Gln Leu
            100                 105                 110

Lys Glu Phe Asn Ala Tyr Phe Lys Phe His Glu Ile Tyr Leu Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Glu Asn Leu Leu Lys Leu Ala Pro
                165                 170                 175
```

```
Asp Phe Lys Asn Asp Arg Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290


<210> SEQ ID NO 12
<211> LENGTH: 291
<212> TYPE: PRT
<213> ORGANISM: Campylobacter jejuni
<220> FEATURE:
<223> OTHER INFORMATION: C. jejuni O:23 ATCC 43449 Cst-II

<400> SEQUENCE: 12

Met Lys Lys Val Ile Ile Ser Gly Asn Gly Pro Ser Leu Lys Glu Ile
  1               5                  10                  15

Asp Tyr Ser Arg Leu Pro Asn Asp Phe Asp Val Phe Arg Cys Asn Gln
             20                  25                  30

Phe Tyr Phe Glu Asp Lys Tyr Tyr Leu Gly Lys Lys Cys Lys Ala Val
         35                  40                  45

Phe Tyr Asn Pro Ser Leu Phe Phe Glu Gln Tyr Tyr Thr Leu Lys His
     50                  55                  60

Leu Ile Gln Asn Gln Glu Tyr Glu Ile Glu Leu Ile Met Cys Ser Asn
 65                  70                  75                  80

Tyr Asn Gln Ala His Leu Glu Asn Glu Asn Phe Val Lys Thr Phe Tyr
                 85                  90                  95

Asp Tyr Phe Pro Asp Ala His Leu Gly Tyr Asp Phe Phe Lys Gln Leu
            100                 105                 110

Lys Glu Phe Asn Ala Tyr Phe Lys Phe His Glu Ile Tyr Phe Asn Gln
        115                 120                 125

Arg Ile Thr Ser Gly Val Tyr Met Cys Thr Val Ala Ile Ala Leu Gly
    130                 135                 140

Tyr Lys Glu Ile Tyr Leu Ser Gly Ile Asp Phe Tyr Asp Asn Gly Gly
145                 150                 155                 160

Gly Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Glu Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Thr Lys
```

```
                245                 250                 255

Asn Ile Asn Phe Lys Lys Ile Lys Ile Lys Glu Asn Ile Tyr Tyr Lys
            260                 265                 270

Leu Ile Lys Asp Leu Leu Lys Leu Pro Ser Asp Ile Lys His Tyr Phe
        275                 280                 285

Lys Gly Lys
    290


<210> SEQ ID NO 13
<211> LENGTH: 291
<212> TYPE: PRT
<213> ORGANISM: Campylobacter jejuni
<220> FEATURE:
<223> OTHER INFORMATION: C. jejuni O:41 ATCC 43460 Cst-II

<400> SEQUENCE: 13

Met Lys Lys Val Ile Ile Ser Gly Asn Gly Pro Ser Leu Lys Glu Ile
  1               5                  10                  15

Asp Tyr Ser Arg Leu Pro Asn Asp Phe Asp Val Phe Arg Cys Asn Gln
             20                  25                  30

Phe Tyr Phe Glu Asp Lys Tyr Tyr Leu Gly Lys Lys Cys Lys Ala Val
         35                  40                  45

Phe Tyr Asn Pro Ser Leu Phe Phe Glu Gln Tyr Tyr Thr Leu Lys His
     50                  55                  60

Leu Ile Gln Asn Gln Glu Tyr Glu Thr Glu Leu Ile Met Cys Ser Asn
 65                  70                  75                  80

Phe Asn Gln Ala His Leu Glu Asn Gln Asn Phe Val Lys Thr Phe Tyr
                 85                  90                  95

Asp Tyr Phe Pro Asp Ala His Leu Gly Tyr Asp Phe Phe Lys Gln Leu
            100                 105                 110

Lys Glu Phe Asn Ala Tyr Phe Lys Phe His Glu Ile Tyr Phe Asn Gln
        115                 120                 125

Arg Ile Thr Ser Gly Val Tyr Met Cys Thr Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Glu Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Thr Lys
                245                 250                 255

Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290


<210> SEQ ID NO 14
```

-continued

<211> LENGTH: 2022
<212> TYPE: DNA
<213> ORGANISM: Artificial Sequence
<220> FEATURE:
<223> OTHER INFORMATION: Description of Artificial Sequence:PST-16
self-priming poly-sialyltransferase fusion of truncated
bi-functional alpha-2,3/alpha-2,8-sialyltransferase (C. jejuni
Cst-II) and poly-sialyltransferase (E. coli APEC O1 orf63 Pst)

<400> SEQUENCE: 14

```
atgaaaaaag ttattattgc tggaaatgga ccaagtttaa aagaaattga ttattcaaga     60

ctaccaaatg attttgatgt atttagatgt aatcaatttt attttgaaga taaatactat    120

cttggtaaaa aatgcaaggc agtattttac aatcctagtc ttttttttga acaatactac    180

actttaaaac atttaatcca aaatcaagaa tatgagaccg aactaattat gtgttctaat    240

tacaaccaag ctcatctaga aaatgaaaat tttgtaaaaa ctttttacga ttattttcct    300

gatgctcatt tgggatatga tttttttcaaa caacttaaag attttaatgc ttattttaaa    360

tttcacgaaa tttatttcaa tcaaagaatt acctcagggg tctatatgtg tgcagtagcc    420

atagccctag gatacaaaga aatttatctt tcgggaattg atttttatca aaatgggtca    480

tcttatgctt ttgatactaa acaaaaaaat cttttaaaat tggctcctaa ttttaaaaat    540

gataattcac actatattgg acatagtaaa aatacagata taaaagcttt agaatttcta    600

gaaaaaactt acaaaaataaa actatattgc ttatgtccta acagtctttt agcaaatttt    660

atagaactag cgccaaattt aaattcaaat tttatcatac aagaaaaaaa taactacact    720

aaagatatac tcataccttc tagtgaggct tatggaaaat tttcaaaaaa tattaatttt    780

ggaggcggac atatgatatt tgatgctagt ttaaagaagt tgaggaaatt atttgtaaat    840

ccaattgggt ttttccgtga ctcatggttt tttaattcta aaaacaaggc tgaagagcta    900

ctatcaccgt taaaaaataaa aagtaaaaat atttttataa ttagtaacct ggggcaatta    960

aaaaaagctg agtcatttgt acaaaaattt agcaagagaa gtaactatct tattgttttg   1020

gcaactgaaa aaaatactga gatgccaaaa attattgttg aacaaataaa taataaatta   1080

ttttcttcat acaaggtact attcattcca actttcccaa atgtttttttc acttaaaaag   1140

gttatatggt tttataacgt atataattat ttagttttaa attcaaaagc taaagatgct   1200

tattttatga gctatgcgca acattatgca atcttcgtat atttgttcaa aaaaaaataat   1260

ataagatgtt cattaattga agaggggaca gggacttata aaaccgaaaa agaaaaccca   1320

gtagtaaata ttaattttta ttcagagatt attaattcaa ttatcttgtt ccattatcca   1380

gatttgaaat ttgaaaatgt atacggtaca tatccaattt tgcttaagaa aaaatttaat   1440

gcgcaaaaat ttgttgagtt taaaggtgct ccatcagtta aatcatcaac cagaatagat   1500

aatgttatcc ataaatattc tataactaga gatgatataa tatatgcaaa tcaaaagtat   1560

ttgattgaac atacattatt tgcggattcg ttaatttcta tcttacttag aatagataag   1620

cctgataatg caagaatatt tataaaacct caccctaaag agcctaaaaa aaatattaat   1680

gcaattcaaa aggcaataaa aaaggcaaaa tgtcgtgaca taattcttat aacagagcca   1740

gactttttaa tagagccggt aataaaaaaa gcaaaaataa aacacttaat tggattaaca   1800

tcatcttctt tggtatatgc acctttagtt tctaaaagat gtcagtctta ttcaatagcg   1860

cctcttatga taaagttgtg tgataatgat aaatcccaaa aagggattaa tacgctgcgt   1920

ctccatttcg atattttaaa gaattttgat aatgttaaaa tattatcgga tgatataaca   1980

tctccctctt tgcacgataa aaggattttc ttgggggagt aa                      2022
```

-continued

<210> SEQ ID NO 15
<211> LENGTH: 673
<212> TYPE: PRT
<213> ORGANISM: Artificial Sequence
<220> FEATURE:
<223> OTHER INFORMATION: Description of Artificial Sequence:PST-16 self-priming poly-sialyltransferase fusion of truncated bi-functional alpha-2,3/alpha-2,8-sialyltransferase (C. jejuni Cst-II) and poly-sialyltransferase (E. coli APEC O1 orf63 Pst)

<400> SEQUENCE: 15

```
Met Lys Lys Val Ile Ile Ala Gly Asn Gly Pro Ser Leu Lys Glu Ile
  1               5                  10                  15

Asp Tyr Ser Arg Leu Pro Asn Asp Phe Asp Val Phe Arg Cys Asn Gln
             20                  25                  30

Phe Tyr Phe Glu Asp Lys Tyr Tyr Leu Gly Lys Lys Cys Lys Ala Val
         35                  40                  45

Phe Tyr Asn Pro Ser Leu Phe Phe Glu Gln Tyr Tyr Thr Leu Lys His
     50                  55                  60

Leu Ile Gln Asn Gln Glu Tyr Glu Thr Glu Leu Ile Met Cys Ser Asn
 65                  70                  75                  80

Tyr Asn Gln Ala His Leu Glu Asn Glu Asn Phe Val Lys Thr Phe Tyr
                 85                  90                  95

Asp Tyr Phe Pro Asp Ala His Leu Gly Tyr Asp Phe Phe Lys Gln Leu
            100                 105                 110

Lys Asp Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Gly Gly Gly His Met Ile Phe Asp Ala Ser Leu Lys
            260                 265                 270

Lys Leu Arg Lys Leu Phe Val Asn Pro Ile Gly Phe Phe Arg Asp Ser
        275                 280                 285

Trp Phe Phe Asn Ser Lys Asn Lys Ala Glu Glu Leu Leu Ser Pro Leu
    290                 295                 300

Lys Ile Lys Ser Lys Asn Ile Phe Ile Ile Ser Asn Leu Gly Gln Leu
305                 310                 315                 320

Lys Lys Ala Glu Ser Phe Val Gln Lys Phe Ser Lys Arg Ser Asn Tyr
                325                 330                 335

Leu Ile Val Leu Ala Thr Glu Lys Asn Thr Glu Met Pro Lys Ile Ile
            340                 345                 350

Val Glu Gln Ile Asn Asn Lys Leu Phe Ser Ser Tyr Lys Val Leu Phe
        355                 360                 365
```

Ile Pro Thr Phe Pro Asn Val Phe Ser Leu Lys Lys Val Ile Trp Phe
370 375 380

Tyr Asn Val Tyr Asn Tyr Leu Val Leu Asn Ser Lys Ala Lys Asp Ala
385 390 395 400

Tyr Phe Met Ser Tyr Ala Gln His Tyr Ala Ile Phe Val Tyr Leu Phe
405 410 415

Lys Lys Asn Asn Ile Arg Cys Ser Leu Ile Glu Glu Gly Thr Gly Thr
420 425 430

Tyr Lys Thr Glu Lys Glu Asn Pro Val Val Asn Ile Asn Phe Tyr Ser
435 440 445

Glu Ile Ile Asn Ser Ile Ile Leu Phe His Tyr Pro Asp Leu Lys Phe
450 455 460

Glu Asn Val Tyr Gly Thr Tyr Pro Ile Leu Leu Lys Lys Lys Phe Asn
465 470 475 480

Ala Gln Lys Phe Val Glu Phe Lys Gly Ala Pro Ser Val Lys Ser Ser
485 490 495

Thr Arg Ile Asp Asn Val Ile His Lys Tyr Ser Ile Thr Arg Asp Asp
500 505 510

Ile Ile Tyr Ala Asn Gln Lys Tyr Leu Ile Glu His Thr Leu Phe Ala
515 520 525

Asp Ser Leu Ile Ser Ile Leu Leu Arg Ile Asp Lys Pro Asp Asn Ala
530 535 540

Arg Ile Phe Ile Lys Pro His Pro Lys Glu Pro Lys Lys Asn Ile Asn
545 550 555 560

Ala Ile Gln Lys Ala Ile Lys Lys Ala Lys Cys Arg Asp Ile Ile Leu
565 570 575

Ile Thr Glu Pro Asp Phe Leu Ile Glu Pro Val Ile Lys Lys Ala Lys
580 585 590

Ile Lys His Leu Ile Gly Leu Thr Ser Ser Ser Leu Val Tyr Ala Pro
595 600 605

Leu Val Ser Lys Arg Cys Gln Ser Tyr Ser Ile Ala Pro Leu Met Ile
610 615 620

Lys Leu Cys Asp Asn Asp Lys Ser Gln Lys Gly Ile Asn Thr Leu Arg
625 630 635 640

Leu His Phe Asp Ile Leu Lys Asn Phe Asp Asn Val Lys Ile Leu Ser
645 650 655

Asp Asp Ile Thr Ser Pro Ser Leu His Asp Lys Arg Ile Phe Leu Gly
660 665 670

Glu

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:FLAG tag, purification tag, epitope tag

<400> SEQUENCE: 16

Asp Tyr Lys Asp Asp Asp Asp Lys
1 5

<210> SEQ ID NO 17
<211> LENGTH: 12
<212> TYPE: PRT
<213> ORGANISM: Artificial Sequence
<220> FEATURE:

```
<223> OTHER INFORMATION: Description of Artificial Sequence:
      bi-functional sialyltransferase motif A
<220> FEATURE:
<221> NAME/KEY: MOD_RES
<222> LOCATION: (12)
<223> OTHER INFORMATION: Xaa = Asp or Glu

<400> SEQUENCE: 17

Asp Val Phe Arg Cys Asn Gln Phe Tyr Phe Glu Xaa
  1               5                  10


<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence:
      bi-functional sialyltransferase motif B

<400> SEQUENCE: 18

Arg Ile Thr Ser Gly Val Tyr Met Cys
  1               5


<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence:
      bi-functional sialyltransferase motif A

<400> SEQUENCE: 19

Asp Val Phe Arg Cys Asn Gln Phe Tyr Phe Glu Asp
  1               5                  10


<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence:
      bi-functional sialyltransferase motif A

<400> SEQUENCE: 20

Asp Val Phe Arg Cys Asn Gln Phe Tyr Phe Glu Glu
  1               5                  10


<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence:PCR
      amplification primer CJ-131

<400> SEQUENCE: 21

cttaggaggt catatgaaaa aagttattat tgctggaaat g                        41


<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence:PCR
      amplification primer CJ-132

<400> SEQUENCE: 22

cctaggtcga cttattttcc tttgaaataa tgctttatat c                        41
```

```
<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer CJ42 in heptosylTase-II

<400> SEQUENCE: 23

gccattaccg tatcgcctaa ccagg                                            25


<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer CJ43 in heptosylTase-I

<400> SEQUENCE: 24

aaagaatacg aatttgctaa agagg                                            25


<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence:epitope tag,
      purification tag, metal chelate affinity
      polyhistidine (poly His) tag, six adjacent
      histidines

<400> SEQUENCE: 25

His His His His His His
  1               5


<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:DDDDK (EC5)
      epitope tag, purification tag

<400> SEQUENCE: 26

Asp Asp Asp Asp Lys
  1               5


<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:polyoma
      middle T protein epitope tag, purification tag

<400> SEQUENCE: 27

Glu Tyr Met Pro Met Glu
  1               5


<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence:E. coli PST
      PCR 5' primer

<400> SEQUENCE: 28
```

aaggtataag acatatgata tttgatgcta gtttaaagaa g 41

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence:E. coli PST
PCR 3' primer

<400> SEQUENCE: 29
cctaggtcga cttactcccc caagaaaatc cttttatcgt gc 42

<210> SEQ ID NO 30
<211> LENGTH: 47
<212> TYPE: DNA
<213> ORGANISM: Artificial Sequence
<220> FEATURE:
<223> OTHER INFORMATION: Description of Artificial Sequence:N.
meningitidis PST PCR amplification 5' primer

<400> SEQUENCE: 30
gctggagctg gacatatgct aaagaaaata aaaaaagctc tttttca 47

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence:N.
meningitidis PST PCR amplification 3' primer

<400> SEQUENCE: 31
gctggagctg gagtcgacct attatctatc tctaccaatt ctattgtc 48

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:
glyco-peptide acceptor
<220> FEATURE:
<221> NAME/KEY: MOD_RES
<222> LOCATION: (4)
<223> OTHER INFORMATION: Xaa = Thr modified by O-linked
alpha-N-acetylgalactose (alpha-O-GalNAc)

<400> SEQUENCE: 32

Val Gly Val Xaa Glu Thr Pro
1 5

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence:Cst-II
OH4384 amplification 5' primer

<400> SEQUENCE: 33
cttaggaggt catatgaaaa aagttattat tgctggaaat g 41

<210> SEQ ID NO 34
<211> LENGTH: 54
<212> TYPE: DNA
<213> ORGANISM: Artificial Sequence
<220> FEATURE:

-continued

```
<223> OTHER INFORMATION: Description of Artificial Sequence:Cst-II
      OH4384 amplification 3' primer

<400> SEQUENCE: 34

gctggagctg gacatatgtc cgcctccaaa attaatattt tttgaaaatt ttcc          54
```